(12) United States Patent
Barnicki et al.

(10) Patent No.: US 10,570,081 B2
(45) Date of Patent: Feb. 25, 2020

(54) PROCESS FOR MAKING FORMIC ACID UTILIZING LOWER-BOILING FORMATE ESTERS

(71) Applicant: Eastman Chemical Company, Kingsport, TN (US)

(72) Inventors: Scott Donald Barnicki, Kingsport, TN (US); Robert Thomas Hembre, Johnson City, TN (US); Sumit Chakraborty, Johnson City, TN (US); Gerald Wayne Ollis, Kingsport, TN (US); Randy Lynn Jennings, Gate City, VA (US); Stijn Van de Vyver, Ghent (BE)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/043,324

(22) Filed: Jul. 24, 2018

(65) Prior Publication Data
US 2019/0039984 A1 Feb. 7, 2019

Related U.S. Application Data

(60) Provisional application No. 62/540,347, filed on Aug. 2, 2017.

(51) Int. Cl.
*C07C 51/09* (2006.01)
*C07C 67/36* (2006.01)
(Continued)

(52) U.S. Cl.
CPC .............. *C07C 51/09* (2013.01); *C07C 51/44* (2013.01); *C07C 51/46* (2013.01); *C07C 67/36* (2013.01)

(58) Field of Classification Search
CPC .......... C07C 51/09; C07C 51/44; C07C 51/46; C07C 67/36
See application file for complete search history.

(56) References Cited

U.S. PATENT DOCUMENTS

| 1,400,195 A | 12/1921 | Willkie |
| 1,857,921 A | 5/1932 | Lazier |

(Continued)

FOREIGN PATENT DOCUMENTS

| CA | 1 238 919 A | 7/1988 |
| EP | 2 599 544 A1 | 6/2013 |

(Continued)

OTHER PUBLICATIONS

Notice of Allowance dated Jun. 5, 2019 received in co-pending U.S. Appl. No. 16/043,308.

(Continued)

*Primary Examiner* — Jafar F Parsa
(74) *Attorney, Agent, or Firm* — Matthew W. Smith

(57) ABSTRACT

Disclosed is a process for recovering formic acid from a formate ester of a $C_3$ to $C_4$ alcohol. Disclosed is also a process for producing formic acid by carbonylating a $C_3$ to $C_4$ alcohol, hydrolyzing the formate ester of the alcohol, and recovering a formic acid product. The alcohol may be dried and returned to the reactor. The process enables a more energy efficient production of formic acid than the carbonylation of methanol to produce methyl formate.

19 Claims, 3 Drawing Sheets

(51) Int. Cl.
*C07C 51/44* (2006.01)
*C07C 51/46* (2006.01)

(56) References Cited

U.S. PATENT DOCUMENTS

| | | | |
|---|---|---|---|
| 1,999,403 A | 4/1935 | Dreyfus | |
| 2,060,880 A | 11/1936 | Lazier | |
| 2,152,182 A | 3/1939 | Ellis et al. | |
| 2,305,104 A | 12/1942 | Pardee, Jr. | |
| 2,504,497 A | 4/1950 | Charles et al. | |
| 2,607,805 A | 8/1952 | Gresham | |
| 3,907,884 A * | 9/1975 | Lynn | C07C 29/095 562/609 |
| 3,911,003 A | 10/1975 | Suzuki | |
| 4,052,424 A | 10/1977 | Vanderspurt | |
| 4,076,594 A | 2/1978 | Buelow et al. | |
| 4,112,245 A | 9/1978 | Zehner et al. | |
| 4,149,009 A | 4/1979 | Yoneoka et al. | |
| 4,214,106 A | 7/1980 | Freudenberger et al. | |
| 4,216,339 A | 8/1980 | Couteau et al. | |
| 4,217,460 A | 8/1980 | Hohenschutz et al. | |
| 4,218,568 A | 8/1980 | Hohenschutz et al. | |
| 4,232,171 A | 11/1980 | Yoneoka et al. | |
| 4,319,037 A | 3/1982 | Yoneoka | |
| 4,326,073 A | 4/1982 | Wolf et al. | |
| 4,366,333 A | 12/1982 | Wilkes | |
| 4,436,835 A | 3/1984 | Horie et al. | |
| 4,440,873 A | 4/1984 | Miyazaki et al. | |
| 4,453,026 A | 6/1984 | Tahara et al. | |
| 4,480,122 A | 10/1984 | Horlenko et al. | |
| 4,511,744 A | 4/1985 | Miyazaki et al. | |
| 4,601,909 A | 7/1986 | Nagoshi | |
| 4,677,234 A | 6/1987 | Bartley | |
| 4,792,620 A | 12/1988 | Paulik et al. | |
| 5,144,062 A | 9/1992 | Chen et al. | |
| 5,194,675 A | 3/1993 | Joerg et al. | |
| 5,206,433 A | 4/1993 | Hohenschutz et al. | |
| 6,376,723 B2 | 4/2002 | Drent et al. | |
| 6,455,742 B1 | 9/2002 | Cortright et al. | |
| 6,841,085 B2 | 1/2005 | Werpy et al. | |
| 6,956,134 B2 | 10/2005 | Liu et al. | |
| 7,615,671 B2 | 11/2009 | Puckette et al. | |
| 8,455,677 B2 | 6/2013 | Nakamura et al. | |
| 8,969,632 B2 | 3/2015 | Norman et al. | |
| 9,040,748 B2 | 5/2015 | Janka et al. | |
| 9,493,395 B2 | 11/2016 | Janka et al. | |
| 2015/0151289 A1 | 6/2015 | Mikhailine et al. | |
| 2015/0274621 A1 | 10/2015 | Fairweather et al. | |
| 2016/0318956 A1 | 11/2016 | Quintaine et al. | |
| 2016/0326202 A1 | 11/2016 | Morris et al. | |

FOREIGN PATENT DOCUMENTS

| | | |
|---|---|---|
| GB | 2 116 552 A | 9/1983 |
| WO | WO 82/03854 A1 | 11/1982 |
| WO | WO 2006/106483 A1 | 10/2006 |
| WO | WO 2006/106484 A1 | 10/2006 |
| WO | WO 2013/079659 A1 | 6/2013 |
| WO | WO 2015/091158 A1 | 6/2015 |
| WO | WO 2017/194663 A1 | 11/2017 |

OTHER PUBLICATIONS

Notice of Allowance dated Aug. 22, 2019 received in U.S. Appl. No. 16/043,329.
Co-pending U.S. Appl. No. 16/043,303, filed Jul. 24, 2018; Chakraborty et al.
Co-pending U.S. Appl. No. 16/043,308, filed Jul. 24, 2018; Chakraborty et al.
Office Action dated Oct. 9, 2018, received in co-pending U.S. Appl. No. 16/043,308.
Co-pending U.S. Appl. No. 16/043,312, filed Jul. 24, 2018; Chakraborty et al.
Co-pending U.S. Appl. No. 16/043,317, filed Jul. 24, 2018; Chakraborty et al.
Notice of Allowance dated Nov. 15, 2018 received in U.S. Appl. No. 16/043,320.
Co-pending U.S. Appl. No. 16/043,320, filed Jul. 24, 2018; Chakraborty et al.
Notice of Allowance dated Nov. 2, 2018 received in U.S. Appl. No. 16/043,320.
Co-pending U.S. Appl. No. 16/043,329, filed Jul. 24, 2018; Barnicki et al.
Wittstock et al.; "Nanoporous Gold Catalysts for Selective Gas-Phase Oxidative Coupling of Methanol at Low Temperature;" Science; 2010; vol. 327; pp. 319-323.
Wang et al.; "Graphene-supported Au—Pd bimetallic nanoparticles with excellent catalytic performance in selective oxidation of methanol to methyl formate;" Chem. Commun., 2013, 49, pp. 8250-8252.
Liu et al.; "Methanol Selective Oxidation to Methyl Formate over $ReO_x/CeO_2$ Catalysts;" Catal. Lett.; 2008; 120; pp. 274-280.
Huang et al.; "Effect of treatment temperature on structures and properties of zirconia-supported ruthenium oxide catalysts for selective oxidation of methanol to methyl formate;" Catalysis Today; 2012; 183; pp. 58-64.
Kaichev et al.; "Selective oxidation of methanol to form dimethoxymethane and methyl formate over a monolayer $V_2O_5/TiO_2$ catalyst;" Journal of Catalysis; 2014; 311; pp. 59-70.
Itagaki et al.; "Transition Metal Homogeneous Catalysis for Liquid-Phase Dehydrogenation of Methanol;" Journal of Molecular Catalysis; 1987; 41; pp. 209-220.
Smith et al.; "The Ruthenium-Catalysed Conversion of Methanol into Methyl Formate;" Journal of Organometallic Chemistry; 1985; 291; pp. C13-C14.
Yang et al.; "Mechanistic study on dehydrogenation of methanol with $[RuCl_2(PR_3)_3]$-type catalyst in homogeneous solutions;" Journal of Molecular Catalysis A: Chemical; 1996; 108; pp. 87-93.
Yamakawa et al.; "Catalytic Reaction of Methanol with a Series of Ruthenium (II) Complexes and the Mechanism of the Formation of Acetic Acid from Methanol Alone;" J. Chem. Soc. Dalton Trans.; 1994; pp. 2265-2269.
Shinoda et al.; "One-step Formation of Methyl Acetate with Methanol used as the Sole Source and Catalysis by Ru"—Sn" Cluster Complexes;" J. Chem. Soc., Chem. Commun.; 1990; pp. 1511-1512.
Kuriyama et al.; "Catalytic Hydrogenation of Esters. Development of an Efficient Catalyst and Processes for Synthesising (R)-1,2-Propanediol and 2-(/-Menthoxy)ethanol;" Org. ProcessRes. Dev.; 2012; 16; pp. 166-171.
Liu et al.; "Towards a Sustainable Synthesis of Formate Salts: Combined Catalytic Methanol Dehydrogenation and Bicarbonate Hydrogenation;" Angew. Chem. Int. Ed.; 2014; 53; pp. 7085-7088.
Alberico et al.; "Selective Hydrogen Production from Methanol with a Defined Iron Pincer Catalyst under Mild Conditions;" Angew. Chem. Int. Ed.; 2013; 52; pp. 14162-14166.
Werkmeister et al.; "Pincer-Type Complexes for Catalytic (De)Hydrogenation and Transfer (De)Hydrogenation Reactions: Recent Progress;" Chem. Eur. J.; 2015; 21; pp. 12226-12250.
Chakraborty et al.; "Nickel and Iron Pincer Complexes as Catalysts for the Reduction of Carbonyl Compounds;" Acc. Chem. Res.; 2015; 48; pp. 1995-2003.
Blum et al.; "Catalytically Reactive Ruthenium Intermediates in the Homogeneous Oxidation of Alcohols to Esters;" Israel Journal of Chemistry; vol. 24; 1984; pp. 144-148.
Blum et al.; "Structure of "$\eta^4$-$Ph_4C_4CO)(CO)_3$Ru—a Catalyst Precursor in H-Transfer and Dehydrogenation Reactions of Alcohols;" Inorganica Chimica Acta; 1985; 97; pp. L25-L26.
Warner et al.; "Shvo's Catalyst in Hydrogen Transfer Reactions;" Top Organomet Chem; 2011; 37; pp. 85-125.
Zhang et al.; "Facile Conversion of Alcohols into Esters and Dihydrogen Catalyzed by New Ruthenium Complexes;" J. Am. Chem. Soc.; 2005; 127; pp. 10840-10841.
Gunanathan et al.; "Direct Conversion of Alcohols to Acetals and H2 Catalyzed by an Acridine-Based Ruthenium Pincer Complex;" J. Am. Chem. Soc.; 2009; 131; pp. 3146-3147.

(56) References Cited

OTHER PUBLICATIONS

Zhang et al.; "Electron-Rich PNP- and PNN-Type Ruthenium(II) Hydrido Borohydride Pincer Complexes. Synthesis, Structure, and Catalytic Dehydrogenation of Alcohols and Hydrogenation of Esters;" Organometallics; 2011; 30; pp. 5716-5724.
Chakraborty et al.; "A Molecular Iron Catalyst for the Acceptorless Dehydrogenation and Hydrogenation of N-Heterocycles;" J. Am. Chem. Soc.; 2014; 136; pp. 8564-8567.
Chakraborty et al.; "Well-Defined Iron Catalysts for the Acceptorless Reversible Dehydrogenation-Hydrogenation of Alcohols and Ketones;" ACS Catal.; 2014; 4; pp. 3994-4003.
Chakraborty et al.; "Iron-Based Catalysts for the Hydrogenation of Esters to Alcohols;" J. Am. Chem. Soc.; 2014; 136; pp. 7869-7872.
Srimani et al.; "Ruthenium Pincer-Catalyzed Cross-Dehydrogenative Coupling of Primary Alcohols with Secondary Alcohols under Neutral Conditions;" Adv. Synth. Catal.; 2012; 354; pp. 2403-2406.
Hu et al.; "Rechargeable Hydrogen Storage System Based on the Dehydrogenative Coupling of Ethylenediamine with Ethanol;" Angew. Chem. Int. Ed.; 2016; 55; pp. 1061-1064.
Kim et al.; "Ruthenium-Catalyzed Urea Synthesis Using Methanol as the C1 Source;" Org. Lett.; 2016; 18; pp. 212-215.
Crabtree, Robert H.; "Resolving Heterogeneity Problems and Impurity Artifacts in Operationally Homogeneous Transition Metal Catalysts;" Chem. Rev.; 2012; 112; pp. 1536-1554.
Gnanadesikan et al.; "Direct Catalytic Asymmetric Aldol-Tishchenko Reaction;" J. Am. Chem. Soc.; 2004; 126; pp. 7782-7783.
Haslam, Edwin; "Tetrahedron Report No. 93—Recent Developments in Methods for the Esterification and Protection of the Carboxyl Group;" Tetrahedron; 1980; vol. 36; pp. 2409-2433.
Gregory et al.; "The Production of Ethyl Acetate From Ethylene and Acetic Acid Using Clay Catalysts;" Clay Minerals; 1983; 18; pp. 431-435.
Goldemberg, José; "Ethanol for a Sustainable Energy Future;" Science; 2007; vol. 315; pp. 808-810.
Wang et al.; "Direct transformation of ethanol to ethyl acetate on Cu/ZrO2 catalyst;" Reac. Kinet. Mech. Cat.; 2010; 101; pp. 365-375.
Inui et al.; "Effective formation of ethyl acetate from ethanol over Cu—Zn—Zr—Al—O catalyst;" Journarl of Molecular Catalysis A: Chemical; 2004; 216; pp. 147-156.
Zonetti et al.; "Chemicals from ethanol—The dehydrogenative route of the ethyl acetate one-pot synthesis;" Journal of Molecular Catalysis A: Chemical; 2011; 334; pp. 29-34.
Medeiros et al.; "The role of water in ethanol oxidation over SnO2-supported molybdenum oxides;" Catalysis Letters; 69; 2000; pp. 79-82.
Gunanathan et al.; "Applications of Acceptorless Dehydrogenation and Related Transformations in Chemical Synthesis;" Science; 2013; vol. 341; pp. 249.
Bertoli et al.; "Osmium and Ruthenium Catalysts for Dehydrogenation of Alcohols;" Organometallics; 2011; 30; pp. 3479-3482.
Nielsen et al.; "Efficient Hydrogen Production from Alcohols under Mild Reaction Conditions;" Angew. Chem. Int. Ed.; 2011; 50; pp. 9593-9597.
Morton et al.; "Molecular Hydrogen Complexes in Catalysis: Highly Efficient Hydrogen Production from Alcoholic Substrates catalyzed by Ruthenium Complexes;" J. Chem. Soc., Chem. Commun.; 1988; pp. 1154-1156.
Nielsen et al.; "Towards a Green Process for Bulk-Scale Synthesis of Ethyl Acetate: Efficient Acceptorless Dehydrogenation of Ethanol;" Angew. Chem. Int. Ed.; 2012; 51; pp. 5711-5713.
Carlini et al.; "Selective synthesis of isobutanol by means of the Guerbet reaction Part 2. Reaction of methanol/ethanol and methanol/ethanol/n-propanol mixtures over copper based/MeONa catalytic systems;" Journal of Molecular Catalysis A: Chemical; 200; 2003; pp. 137-146.
Furukawa et al.; "High Polymerization of Acetaldehyde by Alumina—A New Method of Preparation of Polyether;" Journal of Polymer Science; vol. XXXVI; Issue No. 130; 1959; pp. 546.

Degering et al.; "Polymerization of Acetaldehyde and Crotonaldehyde Catalyzed by Aliphatic Tertiary Amines;" Journal of Polymer Science; vol. VII; No. 6; pp. 653-656.
Teunissen et al.; "Ruthenium catalyzed hydrogenation of dimethyl oxalate to ethylene glycol;" Chem. Commun.; 1997; pp. 667-668.
Zhang et al.; "Efficient Homogeneous Catalytic Hydrogenation of Esters to Alcohols;" Angew. Chem. Int. Ed.; 2006; 45; pp. 1113-1115.
Saudan et al.; "Dihydrogen Reduction of Carboxylic Esters to Alcohols under the Catalysis of Homogeneous Ruthenium Complexes: High Efficiency and Unprecedented Chemoselectivity;" Angew. Chem. Int. Ed.; 2007; 46; pp. 7473-7476.
Dub et al.; "Catalytic Reductive Transformations of Carboxylic and Carbonic Acid Derivatives Using Molecular Hydrogen;" ACS Catal.; 2012; 2; pp. 1718-1741.
Clarke, Matthew L.; "Recent developments in the homogeneous hydrogenation of carboxylic acid esters;" Catal. Sci. Technol.; 2012; 2; pp. 2418-2423.
Chakraborty et al.; "First-row transition metal catalyzed reduction of carbonyl functionalities: a mechanistic perspective;" Dalton Trans.; 2010; 39; pp. 7427-7436.
Zell et al.; "Unprecedented Iron-Catalyzed Ester Hydrogenation. Mild, Selective, and Efficient Hydrogenation of Trifluoroacetic Esters to Alcohols Catalyzed by an Iron Pincer Complex;" Angew. Chem. Int. Ed.; 2014; 53; pp. 4685-4689.
Werkmeister et al.; "Hydrogenation of Esters to Alcohols with a Well-Defined Iron Complex;" Angew. Chem. Int. Ed.; 2014; 53; pp. 8722-8726.
Wang et al.; "The Golden Age of Transfer Hydrogenation;" Chem. Rev.; 2015; 115; pp. 6621-6686.
Lee et al.; "Transfer Hydrogenation of Ketones, Nitriles, and Esters Catalyzed by a Half-Sandwich Complex of Ruthenium;" ChemCatChem; 2015; 7; pp. 107-113.
Dubey et al.; "Catalytic Ester Metathesis Reaction and Its Application to Transfer Hydrogenation of Esters;" ACS Catal.; Jun. 2016; pp. 3998-4002.
Dusselier et al.; "Lactic acid as a platform chemical in the biobased economy: the role of chemocatalysis;" Energy Environ. Sci.; 2013; 6; pp. 1415-1442.
Carnahan et al.; "Ruthenium-catalyzed Hydrogenation of Acids to Alcohols;" Journal of the American Chemical Society; 1955; vol. 77; Issue 14; pp. 3766-3768.
Matteoli et al.; "Structure and catalytic activity of phosphine-substituted ruthenium carbonyl carboxylates;" Journal of Organometallic Chemistry; 498; 1995; pp. 177-186.
https://www.ube•ind.co.jp/ube/en/news/2015/20160316_01.html Ube Industries Licenses DMC Technology and Agrees to Establish Joint Venture for High-Purity DMC.
vom Stein et al.; "Highly Versatile Catalytic Hydrogenation of Carboxylic and Carbonic Acid Derivatives using a Ru-Triphos Complex: Molecular Control over Selectivity and Substrate Scope;" J. Am. Chem. Soc.; 2014; 136; pp. 13217-13225.
Shuklov et al.; "Propane-1,2-diols from Dilactides, Oligolactides, or Poly-L-Lactic Acid (PLLA): From Plastic Waste to Chiral Bulk Chemicals;" Chem. Eur. J.; 2014; 20; pp. 957-960.
Spasyuk et al.; "Acceptorless Dehydrogenative Coupling of Ethanol and Hydrogenation of Esters and Imines;" Organometallics; 2012; 31; pp. 5239-5242.
Fan et al.; "Efficient Hydrogenation of Ethyl Lactate to 1,2-Propanediol over Ru—B/TiO$_2$ in Aqueous Solution;" Chemistry Letters; vol. 37, No. 8; 2008; pp. 852-853.
Zhang et al.; "Aqueous-phase hydrogenation of lactic acid to propylene glycol;" Applied Catalysis A: General; 2001; 219; pp. 89-98.
Adkins et al.; "The Hydrogenation of Esters to Alcohols at 25-150°;" Journal of the American Chemical Society; 1948; vol. 70; Issue 9; pp. 3121-3125.
Broadbent et al.; "Rhenium and Its Compounds as Hydrogenation Catalysts. III. Rhenium Heptoxide;" Journal of Organic Chemistry; 1959; vol. 24; Issue 12; pp. 1847-1854.
Hietala et al.; "Formic Acid"; Ullmann's Encyclopedia of Industrial Chemistry; vol. 16; 2012; Wiley-VCH Verlag GmbH & Co. KGaA, Weinheim; pp. 13-33.

(56) References Cited

OTHER PUBLICATIONS

Di Girolamo et al.; "Acidic and basic ion exchange resins for industrial applications;" Journal of Molecular Catalysis A: Chemical; 2001; 177; pp. 33-40.
Nørskov et al.; "Towards the computational design of solid catalysts;" Nature Chemistry; vol. 1; Apr. 2009; pp. 37-46.
Bielinski et al.; "Base-Free Methanol Dehydrogenation Using a Pincer-Supported Iron Compound and Lewis Acid Co-catalyst;" ACS Catal.; 2015; 5; pp. 2404-2415.
Fairweather et al.; "Homogeneous Hydrogenation of Fatty Acid Methyl Esters and Natural Oils under Neat Conditions;" Organometallics; 2015; 34; pp. 335-339.
Qu et al.; "Computational Mechanistic Study of Fe-Catalyzed Hydrogenation of Esters to Alcohols: Improving Catalysis by Accelerating Precatalyst Activation with a Lewis Base;" ACS Catal.; 2014; 4; pp. 4377-4388.
Notification of Transmittal of the International Search Report and the Written Opinion of the International Searching Authority with dated Oct. 19, 2018 for International Application No. PCT/US2018/044482.
Notification of Transmittal of the International Search Report and the Written Opinion of the International Searching Authority with dated Oct. 19, 2018 for International Application No. PCT/US2018/044485.
Monnereau et al.; "Efficient Synthesis of Differentiated syn-1,2-Diol Derivatives by Asymmetric Transfer Hydrogenation-Dynamic Kinetic Resolution of α-Alkoxy-Substituted β-Ketoesters;" Chemistry—A European Journal; 2015; 21; pp. 11799-11806.
Kim et al.; "Transfer Hydrogenation of Organic Formates and Cyclic Carbonates: An Alternative Route to Methanol from Carbon Dioxide;" ACS Catal.; 2014; 4; pp. 3630-3636.
Patil et al.; "Immobilized Iron Metal-Containing Ionic Liquid-Catalyzed Chemoselective Transfer Hydrogenation of Nitroarenes into Anilines;" ACS Sustainable Chem. Eng.; 2016; 4; pp. 429-436.
Notification of Transmittal of the International Search Report and the Written Opinion of the International Searching Authority with dated Oct. 19, 2018 for International Application No. PCT/US2018/044476.
Notification of Transmittal of the International Search Report and the Written Opinion of the International Searching Authority with dated Oct. 26, 2018 for International Application No. PCT/US2018/044518.
Pandey et al.; "Acceptorless Alcohol Dehydrogenation: A Mechanistic Perspective;" Proc. Natl. Acad. Sci., India, Sect. A Phys. Sci.; 2016; vol. 86; Issue 4; pp. 561-579.
Notification of Transmittal of the International Search Report and the Written Opinion of the International Searching Authority dated Oct. 26, 2018 for International Application No. PCT/US2018/044512.
Iranpoor et al.; "Silphos [PCl$_{3-n}$(SiO$_2$)$_n$]: a heterogeneous phosphine reagent for formylation and acetylation of alcohols and amines with ethyl formate and acetate;" Tetrahedron Letters; 46; 2005; pp. 7963-7966.
Lane et al.; "Iron-Catalyzed Amide Formation from the Dehydrogenative Coupling of Alcohols and Secondary Amines;" Organometallics; 2017; 36; pp. 2020-2025.
Notification of Transmittal of the International Search Report and the Written Opinion of the International Searching Authority dated Oct. 26, 2018 for International Application No. PCT/US2018/044506.
Notification of Transmittal of the International Search Report and the Written Opinion of the International Searching Authority dated Nov. 6, 2018 for International Application No. PCT/US2018/044521.
Notice of Allowance dated Mar. 7, 2019 received in U.S. Appl. No. 16/043,317.
Notice of Allowance dated Mar. 7, 2019 received in U.S. Appl. No. 16/043,320.
Office Action dated Apr. 5, 2019 received in U.S. Appl. No. 16/043,329.
Chintan et al.; "Separation of azeotropic mixture of formic acid-water by using Li—Br as a salt by extractive distillation;" IJARIIE-ISSN (O)-2395-4396; vol. 2; Issue 3; 2016; pp. 607-612.

* cited by examiner

PROCESS FOR MAKING FORMIC ACID UTILIZING LOWER-BOILING FORMATE ESTERS

CROSS REFERENCE TO RELATED APPLICATION

This application claims the benefit of Provisional Application 62/540,347 filed on Aug. 2, 2017 under 35 U.S.C. § 119(e)(1), the entire content of which is incorporated herein by reference.

TECHNICAL FIELD

This invention pertains to the recovery of formic acid from a formate ester mixture, wherein the formate ester mixture is hydrolyzed to produce formic acid and an alcohol. More particularly, the invention pertains to a process for recovering formic acid from a formate ester of a $C_3$ to $C_4$ alcohol. Producing formic acid via the carbonylation of a $C_3$ to $C_4$ alcohol can lead to significant energy usage savings compared to the traditional carbonylation of methanol to methyl acetate.

BACKGROUND

The synthesis of formic acid from either carbon monoxide and water or carbon dioxide and hydrogen is thermodynamically highly unfavorable and is not a practiced industrial approach to formic acid synthesis. In an effort to overcome these limitations, formic acid has been produced industrially by a number of indirect methods, requiring complicated multi-step reaction and separation sequences, with high capital and energy costs (Reutemann, W.; Kieczka, H., "Formic Acid", in Ullmann's Encyclopedia of Industrial Chemistry, Volume 16, 2012, Wiley-VCH Verlag GmbH & Co. KGaA, Weinheim, pp. 13-33). One such method is the acidification of formate salts, produced for example, as a by-product of the Cannizzaro reaction for the production of formaldehyde/aldehyde-based polyols such as trimethylolpropane. This method results in the generation of a salt such as sodium sulfate, with corresponding disposal issues.

The production of formic acid by hydrolysis of formamide, formed by a three-step process involving carbonylation of methanol to methyl formate, reaction with ammonia to produce formamide, followed by hydrolysis-salt formation, is another commercial approach to formic acid synthesis. However, the consumption of ammonia and sulfuric acid, along with the unavoidable production of ammonium sulfate, have made this process economically inferior.

The predominant industrial process for the production of formic acid is via base-catalyzed carbonylation of methanol to methyl formate, followed by hydrolysis of methyl formate to methanol and formic acid, and subsequent separation of water, methanol, and unreacted methyl formate from liberated free formic acid. This process suffers from many drawbacks. Although readily carbonylated, methanol conversion is relatively low (typically less than 30%) at economically viable temperatures and CO pressures. Methyl formate must be distilled from unconverted methanol and the active base catalyst without reversion of the formate back to CO and methanol. The hydrolysis of methyl formate is thermodynamically unfavorable, resulting in only 25-30% conversion, even at a molar ratio of water/ester of 2/1 or higher. If conventional distillation is used to process the hydrolysis reactor effluent, all of the unreacted methyl formate and by-product methanol must be distilled overhead, since formic acid is higher boiling than methyl formate and methanol. The low conversion leads to high recycle ratios of unreacted methyl formate to produced formic acid (typically 3-4 tons of recycled methyl formate per ton of formic acid produced).

Distillation of a hydrolysis reactor effluent (with methanol and methyl formate taken overhead) also produces an underflow that is relatively dilute formic acid in water (typically less than 40 wt. % formic acid), and since formic acid and water form a maximum-boiling azeotrope, the separation of formic acid from water is a relatively energy and capital intensive endeavor. The conventional approach to formic acid-water separation is pressure-swing distillation, whereas the composition of the water/formic acid azeotrope varies fairly significantly with pressure. For example, the water/formic acid wt/wt ratio is about 42/58 at 0.04 bara, 40/60 at 0.067 bara, 25/75 at 1.013 bara, 20/80 at 2.03 bara, 17/83 at 3.04 bara, and 16/84 at 4.05 bara. In the pressure swing distillation system, water is distilled overhead in a first high pressure column, and the maximum boiling formic acid-water azeotrope is taken as a bottoms product. The azeotrope is then further distilled in a second low pressure column with typically 90-99% formic acid as distillate, and a new maximum-boiling azeotrope composition taken as underflow, which is recycled to the high-pressure column. Thus, all the water entering the two-column system with the feed eventually exits as part of the distillate in the high-pressure column. Although the distillate from the high-pressure column can be used for heat integration purposes (either to generate steam upon condensing or directly as a condensing heat source), this pressure swing distillation is very energy intensive, requiring typically 3 to 5 tons of steam per ton of formic acid produced as high purity formic acid.

Several methods have been proposed to improve both the hydrolysis conversion of methyl formate to formic acid and methanol and the separation of formic acid-water. Extraction processes have been proposed for improving the energy consumption for separating formic acid and water, as for example using secondary amides (Hohenschutz et al, U.S. Pat. No. 4,217,460, Aug. 12, 1980, and Wolf et al, U.S. Pat. No. 4,326,073, Apr. 20, 1982). These processes introduce new contaminants into the system and require relatively high vacuum distillation and high energy consumption to separate formic acid from the extractant. Hohenschutz et al, proposed adding a tertiary nitrogen base (U.S. Pat. No. 4,218,568, Aug. 19, 1980) or weak base formamide derivative (U.S. Pat. No. 5,206,433, Apr. 27, 1993) directly to the hydrolysis reaction mixture to shift the equilibrium conversion by forming a salt of the base and formic acid. Such methods also require considerable energy to decompose the salt and liberate formic acid. Buelow et al (U.S. Pat. No. 4,076,594, Feb. 28, 1978) discloses the use of basic extractive distillation agents for separation of formic acid and water, but water must still be distilled overhead and the base-formic acid complex decomposed, resulting again in high energy usage.

Conventional carbonylation-hydrolysis processes utilizing methanol as the alcohol and distillative separation techniques or processes utilizing basic extractants, reactants, or extractive distillation agents are capital and energy intensive. Thus, there is a need for lower energy process for synthesis of formic acid which overcomes these deficiencies.

BRIEF SUMMARY

In an embodiment, a process for recovering formic acid from a formate ester mixture comprises feeding the formate ester mixture, a hydrolysis recycle, and water to a hydrolysis zone. The formate ester mixture comprises a formate ester of an alcohol. The process comprises hydrolyzing the formate ester of the alcohol, and removing a hydrolysis effluent comprising the formate ester of the alcohol, formic acid, and the alcohol. The process further comprises feeding the hydrolysis effluent to a distillation zone and removing a formic acid product and a wet alcohol mixture. The formic acid product comprises greater than 75 wt. % formic acid. The wet alcohol mixture comprises the alcohol, water, the formate ester of the alcohol, and less than 0.5 wt. % formic acid. The process further comprises feeding the wet alcohol mixture to an alcohol recovery zone and removing a dry alcohol stream and the hydrolysis recycle. The dry alcohol stream comprises the alcohol and less than 1 wt. % water and the hydrolysis recycle comprises water, the formate ester of the alcohol, and/or the alcohol. The alcohol is selected from the group consisting of $C_3$ to $C_4$ alcohols.

In another embodiment, a process for producing formic acid comprises feeding carbon monoxide, a fresh feed, and a catalyst feed, to a carbonylation zone. The fresh feed comprises an alcohol and the catalyst feed comprises a homogeneous catalyst. The process comprises carbonylating the alcohol to produce a formate ester of the alcohol, and removing a carbonylation effluent. The carbonylation effluent comprises the formate ester of the alcohol, the alcohol, and the homogeneous catalyst. The process further comprises feeding the carbonylation effluent to a catalyst separation zone and removing a catalyst mixture and a formate ester mixture. The catalyst mixture comprises the homogeneous catalyst and the alcohol and the formate ester mixture comprises the formate ester of the alcohol. The process further comprises feeding the formate ester mixture, a hydrolysis recycle, and water to a hydrolysis zone, hydrolyzing the formate ester of the alcohol, and removing a hydrolysis effluent. The hydrolysis effluent comprises the formate ester of the alcohol, formic acid, and the alcohol. The process further comprises feeding the hydrolysis effluent to a distillation zone and removing a formic acid product and a wet alcohol mixture. The formic acid product comprises greater than 75 wt. % formic acid and the wet alcohol mixture comprises the alcohol, water, the formate ester of the alcohol, and less than 0.5 wt. % formic acid. The process further comprises feeding the wet alcohol mixture to an alcohol recovery zone and removing a dry alcohol stream and the hydrolysis recycle stream. The dry alcohol stream comprises the alcohol and less than 1 wt. % water. The hydrolysis recycle stream comprises water, the formate ester of the alcohol, and/or the alcohol. The alcohol is selected from the group consisting of $C_3$ to $C_4$ alcohols.

In yet another embodiment, a process for producing formic acid comprises feeding methanol, a dry alcohol stream, and a catalyst recycle to a dehydrogenative coupling (DHC) zone. The dry alcohol stream comprises the alcohol and less than 1 wt. % water. The process comprises performing a DHC reaction of methanol with the alcohol to produce a formate ester of the alcohol and hydrogen, and removing a DHC effluent. The DHC effluent comprises the formate ester of the alcohol and a homogeneous catalyst. The process further comprises feeding the DHC effluent to a catalyst separation zone and removing the catalyst recycle and a formate ester mixture. The catalyst recycle comprises the homogeneous catalyst and the formate ester mixture comprises the formate ester of the alcohol. The process further comprises feeding the formate ester mixture, a hydrolysis recycle, and water to a hydrolysis zone, hydrolyzing the formate ester of the alcohol, and removing a hydrolysis effluent. The hydrolysis effluent comprises the formate ester of the alcohol, formic acid, and the alcohol. The process further comprises feeding the hydrolysis effluent to a distillation zone and removing a formic acid product and a wet alcohol mixture. The formic acid product comprises greater than 75 wt. % formic acid, and the wet alcohol mixture comprises the alcohol, water, the formate ester of the alcohol, and less than 0.5 wt. % formic acid. The process further comprises feeding the wet alcohol mixture to an alcohol recovery zone and removing a dry alcohol stream and the hydrolysis recycle. The hydrolysis recycle comprises water, the formate ester of the alcohol, and/or the alcohol. The alcohol is selected from the group consisting of iso-propanol, 2-butanol, and tert-butanol.

DETAILED DESCRIPTION

Figure 1:
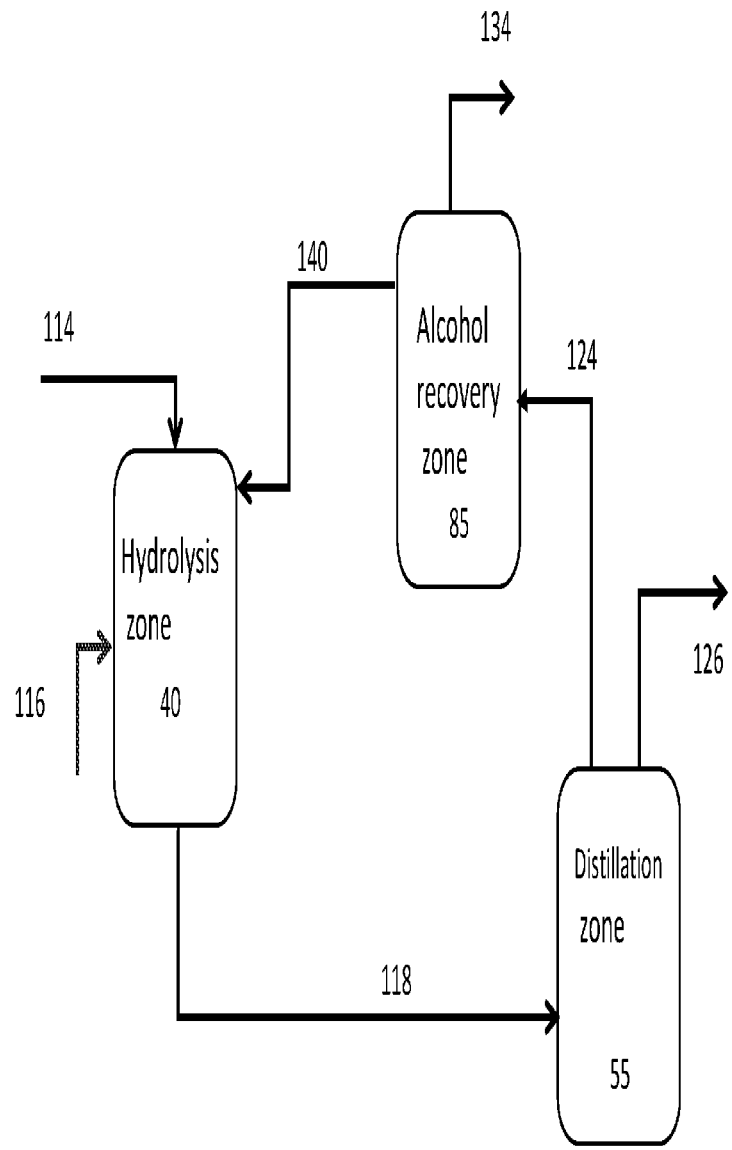
FIG. 1 illustrates a non-limiting process flow diagram of the recovery of formic acid from a formate ester mixture.

In an embodiment, a process for recovering formic acid from a formate ester mixture comprises feeding the formate ester mixture, a hydrolysis recycle, and water to a hydrolysis zone. The formate ester mixture comprises a formate ester of an alcohol. The process comprises hydrolyzing the formate ester of the alcohol, and removing a hydrolysis effluent comprising the formate ester of the alcohol, formic acid, and the alcohol. The process further comprises feeding the hydrolysis effluent to a distillation zone and removing a formic acid product and a wet alcohol mixture. The formic acid product comprises greater than 75 wt. % formic acid. The wet alcohol mixture comprises the alcohol, water, the formate ester of the alcohol, and less than 0.5 wt. % formic acid. The process further comprises feeding the wet alcohol mixture to an alcohol recovery zone and removing a dry alcohol stream and a hydrolysis recycle. The dry alcohol stream comprises the alcohol and less than 1 wt. % water and the hydrolysis recycle comprises water, the formate ester of the alcohol, and/or the alcohol. The alcohol is selected from the group consisting of $C_3$ to $C_4$ alcohols.

Unless otherwise indicated, all numbers expressing quantities of ingredients, properties such as molecular weight, reaction conditions, and so forth used in the specification and claims are to be understood as being modified in all instances by the term "about."

As used herein, the indefinite articles "a" and "an" mean one or more, unless the context clearly suggests otherwise. Similarly, the singular form of nouns includes their plural form, and vice versa, unless the context clearly suggests otherwise.

It is to be understood that the mention of one or more process steps does not preclude the presence of additional process steps before or after the combined recited steps or intervening process steps between those steps expressly identified. It is also to be understood that the feeding of a process flow to a zone of the process or the removing of a process flow from the process includes the feeding or removing of a portion of the process flow and/or the entire process flow, unless otherwise indicated. Moreover, the lettering of process steps or ingredients is a convenient means for identifying discrete activities or ingredients and the recited lettering can be arranged in any sequence, unless otherwise indicated.

As used herein the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The term "boiling point temperature", as used herein, refers to the temperature of a substance at which the vapor pressure of the liquid equals the operating pressure and the liquid changes into a vapor. The terms, "higher boiling point temperature", "boiling point temperature higher than" or "compound A has a boiling point temperature higher than compound B", as used herein, refers to a substance being at a higher temperature before the vapor pressure of the liquid equals the operating temperature.

The term, "carbonylation zone", as used herein, refers to a part of a process wherein the "alcohol" is carbonylated. The term, "carbonylating", as used herein refers the reaction of an alcohol with carbon monoxide. The term, "carbonylation effluent", as used herein, refers to the effluent from the "carbonylation zone". The term, "catalyst separation zone", as used herein, may refer to a part of a process wherein the "homogeneous catalyst" is separated, via a vapor-liquid equilibrium based process operation, from the "carbonylation effluent". The term, "catalyst mixture', as used herein, refers to the stream leaving the "catalyst separation zone" which is rich in the "homogeneous catalyst". The "catalyst mixture" may be further processed and/or fed to the "carbonylation zone".

The term, "dehydrogenative coupling zone" or "DHC zone", as used herein, refers to a part of a process wherein a dehydrogenative couple reaction of methanol and the "alcohol" is performed. The term, "dehydrogenative coupling effluent" or "DHC effluent", as used herein, refers to the effluent from the "DHC zone". The term, "catalyst separation zone", as used herein, may refer to a part of the process wherein the "homogeneous catalyst" is separated from the "DHC effluent". The term, "catalyst recycle", as used herein refers to the stream leaving the "catalyst separation zone" which is rich in the "homogenous catalyst" and recycled to the "DHC zone".

The term, "alcohol", as used herein, refers to $C_3$ to $C_4$ alcohols. Non-limiting examples include iso-propanol, 2-butanol, and tert-butanol. The term, "wet alcohol mixture" refers to the process stream comprising water, alcohol, and formate ester of the alcohol which is separated from the hydrolysis effluent in the distillation zone. The term, "alcohol recovery zone", as used herein, refers to the part of the process wherein the "wet alcohol mixture" is separated via fractional distillation into a dry alcohol stream and a hydrolysis recycle.

The term, "distillation zone", as used herein, refers to the part of the process wherein the formic acid is distilled from the other components. In some aspects, the formate ester of the alcohol undergoes further hydrolysis in the "distillation zone". The "distillation zone" comprises at least one "distillation column". The term "distillation column", as used herein, refers to a multi-stage fractionation unit operation wherein the formic acid is separated from a mixture and the separation occur across the multi-stage unit. The term "distillate", as used herein, refers to the stream leaving the top of the "distillation column" (often after having been liquefied in a condenser). The term "bottoms", as used herein, refers to the stream leaving the bottom or base of the "distillation column". The "base temperature" as used herein, refers to the temperature as measured at or near the bottom of a "distillation column", for example, at the base of the column, or of the "bottoms" as it leaves the "distillation column". The term "stages", as used herein, refers to a vapor-liquid contacting device where bubbles of vapor are distributed into a holding volume of boiling liquid. Liquid and vapor flow in counter-current directions. A "lower stage" of the "distillation column" is closer to the bottom and a "higher stage" is closer to the top.

The term, "formate ester", as used herein, refers to an ester for the formula (H—C—O—O—R). The term "formate ester of an alcohol", as used herein, refers to a formate ester wherein the alcohol is the product of hydrolysis of the formate ester. In other words, the reaction of the "formate ester of an alcohol" with water produces an equilibrium mixture with formic acid and the "alcohol". It may also refer to the specific formate ester produced by the carbonylation of an alcohol or dehydrogenative coupling (DHC) of methanol with an alcohol. The term, "formate ester mixture", as used herein, refers to a process stream comprising the "formate ester of an alcohol" and may also comprise the "alcohol".

The term, "formic acid product", as used herein, refers to a process stream comprising the purified formic acid. Typically, commercial grades of formic acid comprises between 75 wt. % and 99 wt. % formic acid.

The term "fresh feed", as used herein, refers to a raw material input to the "carbonylation zone" or "DHC zone" that is new to the process, i.e., it is not a recycle stream. The term "catalyst feed", as used herein refers to the input of the homogeneous catalyst to the "carbonylation zone". The "catalyst feed" may comprise catalyst recycled from the "catalyst separation zone".

The term, "homogeneous catalyst", as used herein, refers to a catalyst that is soluble or partly soluble in the reaction mixture under reaction conditions. For a process comprising carbonylation, particularly useful catalysts include alkali metal alkoxides of the alcohol. For processes comprising dehydrogenative coupling (DHC) of methanol with an alcohol, iron-based catalysts supported by pincer ligands are useful catalysts.

The "hydrolysis zone" is a part of the process wherein the formate ester mixture is hydrolyzed without a separation of components that would impact the equilibrium-limited hydrolysis reaction. The term "hydrolyzing", as used herein, refers to the reaction of an ester with water. The term "hydrolysis reactor", as used herein, refers to the equipment wherein at least part of the hydrolysis reaction occurs. The term, "hydrolysis effluent", as used herein, refers to the effluent from the hydrolysis reaction zone and/or hydrolysis reactor.

The term, "maximum-boiling azeotrope", as used herein, refers to a mixture of at least two components whose proportions cannot be altered by simple distillation, wherein the boiling point of the mixture is higher than the boiling point of any of the components. The term, "minimum-boiling azeotrope", as used herein, refers to a mixture of at least two components whose proportions cannot be altered by simple distillation, wherein the boiling point of the mixture is lower than the boiling point of any of the components. The term, "azeotrope boiling point temperature", as used herein refers to the temperature at which a mixture of at least two components boils with the composition of the liquid and vapor being the same. Formic acid and water form a maximum-boiling azeotrope at temperatures and pressures of industrial interest. The term "formic acid in an amount within x weight percentage points of an amount of formic acid in a formic acid/water azeotrope", as used herein, refers to that the weight percent formic acid/water azeotrope minus the weight percent of formic acid in a formic acid stream at the given conditions being within x percentage points. For example, if at the operating pressure of the distillation column, the formic acid/water azeotrope comprises 80 wt. % formic acid, and the bottoms comprises 84 wt. % formic acid, then the weight percent formic acid in the bottoms is within 4 percentage points (84-80) of the azeotrope. When approaching the azeotrope from the other direction, if at the operating pressure of the distillation column, the formic acid/water azeotrope comprises 80 wt. % formic acid, and the bottoms comprises 75 wt. % formic acid, then the weight percent formic acid in the bottoms is within 5 percentage points (80-75) of the azeotrope.

The term, "molar ratio", as used herein, refers to the moles of one component divided by the moles of another component. For example, if the molar ratio of water to iso-propyl formate is 2:1, then for every mole of iso-propyl formate there are 2 moles of water.

The term, "n-component", as used herein, refers to the number of different type of chemical compounds involved. For example, a 3-component mixture has three chemical compounds. A 2-component azeotrope is an azeotrope formed by two chemical compounds.

The term, "operating pressure" as used herein, refers to the pressure or pressure range of a zone or a piece of equipment when a processing step, such as a reaction or a separation, occurs. The "operating pressure" of a distillation column refers to the pressure as measured at or near the top of the distillation column, for example, at the condenser or at the vacuum pump.

The term, "overall conversion", as used herein, refers to the moles of formic acid in the formic acid product leaving the process from the distillation zone divided by the sum of the moles of formic acid and formate ester of the alcohol in the formate ester mixture, multiplied by 100. The term "hydrolysis conversion", as used herein, refers to the moles of formic acid in the hydrolysis effluent divided by the sum of the moles of formic acid and formate ester of the alcohol in the formate ester mixture plus the moles of formic acid and formate ester of the alcohol in any other feeds to the hydrolysis zone, multiplied by 100. The term, "distillation conversion", as used herein, refers the moles of formic acid in the formic acid product leaving the distillation zone plus the moles of formic acid in any other effluents from the distillation zone, divided by the sum of the moles of formic acid and formate ester of the alcohol in the hydrolysis effluent, multiplied by 100. The term "overall conversion is x to y percentage points higher than hydrolysis conversion", as used herein means that the overall conversion minus the hydrolysis conversion is x to y. For example, if the overall conversion is 80% and it is 20 to 30 percentage points higher than the hydrolysis conversion, then the hydrolysis conversion is 50% to 60%.

In the present embodiment, a process for recovering formic acid from a formate ester mixture comprises feeding the formate ester mixture, a hydrolysis recycle, and water to a hydrolysis zone. The formate ester mixture comprises a formate ester of an alcohol. The alcohol and formic acid are produced when the formate ester of the alcohol is hydrolyzed.

The process by which the formate ester of the alcohol is made is not particularly limited. In one aspect, the formate ester of the alcohol is produced by the carbonylation of the alcohol with carbon monoxide. In another aspect, the formate ester of the alcohol is produced by Baeyer-Villiger oxidation of an aldehyde (e.g., oxidation of isobutyraldehyde to produce isopropyl formate). In another aspect, the formate ester of an alcohol is produced by transesterification of methyl formate with the alcohol. In yet another aspect, the formate ester is produced by the dehydrogenative coupling (DHC or dehydrocoupling) reaction of methanol with a secondary or tertiary alcohol.

In one aspect, the formate ester of the alcohol is selected from the group consisting of n-propyl formate, iso-propyl formate, n-butyl formate, iso-butyl formate, 2-butyl formate, and tert-butyl formate. In one aspect, the formate ester of the alcohol is selected from the group consisting of iso-propyl formate, 2-butyl formate, and tert-butyl formate. In one aspect, the formate ester of the alcohol is selected from the group consisting of iso-propyl formate and 2-butyl formate. In one aspect, the formate ester of the alcohol is iso-propyl formate. In one aspect, the formate ester of the alcohol is 2-butyl formate.

In one aspect, the alcohol is selected from the group consisting of n-propanol, iso-propanol, n-butanol, iso-butanol, 2-butanol, and tert-butanol. In one aspect, the alcohol is selected from the group consisting of iso-propanol, 2-butanol, and tert-butanol. In one aspect, the alcohol is selected from the groups consisting of iso-propanol and 2-butanol. In one aspect, the alcohol is iso-propanol. In one aspect, the alcohol is 2-butanol.

In one aspect, the formate ester mixture comprises 10 wt. % to 99 wt. % formate ester of the alcohol. Other examples of the amount of formate ester of the alcohol in the formate ester mixture include 10 wt. % to 90 wt. %, 10 wt. % to 75 wt. %, 10 wt. % to 50 wt. %, 25 wt. % to 99 wt. %, 25 wt. % to 75 wt. %, 50 wt. % to 99 wt. %, and 50 wt. % to 90 wt. %. In one aspect, the formate ester mixture comprises at least 10 wt. % formate ester of the alcohol. Other examples of the amount of formate ester of the alcohol in the formate ester mixture include at least 15 wt. %, 20 wt. %, 25 wt. %, 45 wt. %, 50 wt. %, 75 wt. %, and 90 wt. % formate ester of the alcohol.

The process of the present embodiment comprises feeding the formate ester mixture, a hydrolysis recycle, and water to a hydrolysis zone. The manner in which the formate ester mixture, hydrolysis recycle, and water are fed to the hydrolysis zone is not particularly limited. In one example, the formate ester mixture, the hydrolysis recycle, and the water are fed separately to the hydrolysis zone. In another example, two or more of the formate ester mixture, hydrolysis recycle, and water may be combined before being fed to the hydrolysis zone.

Within the hydrolysis zone, the formate ester of the alcohol is hydrolyzed to produce the alcohol and formic acid. The formate ester mixture, hydrolysis recycle, and water are fed to the hydrolysis reaction zone wherein the formate ester of the alcohol is hydrolyzed, producing a hydrolysis effluent. The hydrolysis effluent comprises the formate ester of the alcohol, formic acid, water, and the alcohol.

Increasing the amount of water pushes the equilibrium reaction in favor of higher conversion to formic acid. Too large an amount of water, however, can negatively impact the energy usage of the downstream distillation. For example, if the hydrolysis effluent is fed to a distillation column, the amount of water that leaves the bottoms of the column is limited by the maximum-boiling formic acid/water azeotrope. Excess water will be boiled overhead and leave the distillation zone in the wet alcohol mixture, be fed to the alcohol recovery zone, and return to the hydrolysis zone as the hydrolysis recycle.

The formate ester mixture, the hydrolysis recycle, and water are fed to the hydrolysis zone. One skilled in the art recognizes that controlling the total amount of water fed to the hydrolysis zone (whether the water is in a fresh feed or recycle) relative to the amount of the formate ester of the alcohol can impact the equilibrium hydrolysis reaction. Therefore, the ratio of water to formate ester of the alcohol is based upon all streams fed to the hydrolysis zone. In one aspect, the molar ratio of water to formate ester of the alcohol fed to the hydrolysis zone ranges from 0.5:1 to 3:1. Other examples of the molar ratio of water to formate ester of the alcohol ranges are from 0.5:1 to 1.5:1, or 0.5:1 to 1.4:1, or 0.5:1 to: 1.3, or 0.8:1 to 2.4:1, or 1:1 to 2:1, or 1:1 to 1.5:1, or 1.2:1 to 2:1.

The operating conditions for the hydrolysis zone are not particularly limited. Hydrolysis zone temperatures can range from 40° C. to 150° C. Other examples of the hydrolysis zone temperature include 80° C. to 140° C. and 90° C. to 130° C. Hydrolysis zone operating pressure can range from 1 bara to 40 bara. Other examples of hydrolysis zone operating pressure ranges include 1 bara to 30 bara, 2 bara to 30 bara, and 3 bara to 20 bara. The hydrolysis reaction can be autocatalyzed by the formic acid. In one aspect, no component is added (e.g., homogeneous catalyst) to or included in (e.g., a heterogeneous catalyst) the hydrolysis zone. In one aspect, the rate of hydrolysis can be increased by adding an acidic catalyst. Examples of acid catalysts include formic acid (at least 1 mole % added based on moles of formate ester of the alcohol in the formate ester mixture), and heterogeneous catalysts such as sulfonic acid containing resins, PFSA, and kieselguhr.

The hydrolysis zone comprises process equipment within which the hydrolysis reaction occurs. The process equipment is not particularly limited and is sized to give enough residence time to reach the desired conversion in hydrolysis. The process equipment may include one or more of a pipe, a horizontal or vertical reactor, a stirred tank reactor, a pump around loop reactor, or combinations thereof. Heat transfer area may be provided to heat or cool the contents of the hydrolysis equipment.

The process of the present invention may be conducted under continuous, semi-continuous, or batch modes of operation. The term "continuous", as used herein, refers to a process wherein reactants are introduced and products withdrawn simultaneously in an uninterrupted manner. By "continuous" it is meant that the process is substantially or completely continuous in operation and is to be contrasted with a "batch" process. "Continuous" is not meant in any way to prohibit normal interruptions in the continuity of the process due to, for example, start up, reactor maintenance, or scheduled shut down periods. The term "batch" process as used herein means a process wherein all the reactants are added to the hydrolysis zone and then processed according to a predetermined course of reaction during which no material is fed into or removed from the hydrolysis zone. The term "semi-continuous" means a process where some of the reactants are charged at the beginning of the process and the remaining reactants are fed continuously as the reaction progresses.

The process comprises feeding the hydrolysis effluent to a distillation zone and removing a formic acid product and a wet alcohol mixture.

In one aspect, the formic acid product comprises greater than 78 wt. % formic acid. In other examples the formic acid product comprises greater than 75 wt. %, 78 wt. %, 80 wt. %, 82 wt. %, 90 wt. %, 94 wt. %, 95 wt. %, 97 wt. % or 99 wt. % formic acid. In one aspect, the wet alcohol mixture comprises the alcohol, water, the formate ester of the alcohol, and less than 0.5 wt. % formic acid. In other examples, the wet alcohol mixture comprises less than 0.1 wt. %, 500 ppm, or 200 ppm formic acid.

In one aspect, the distillation zone comprises a first distillation column. The process further comprises feeding the hydrolysis effluent to the first distillation column and removing a first distillate and a first bottoms. The first distillate comprises the wet alcohol mixture. The first bottoms comprises formic acid in an amount within 9 weight percentage points of an amount of formic acid in a formic acid/water azeotrope at an operating pressure of the first distillation column. In other examples, the first bottoms comprises formic acid in the amount within 7.5 weight percentage points, 7.0 weight percentage points, or 5.0 weight percentage points of the amount of formic acid in the formic acid/water azeotrope at the operating pressure of the first distillation column.

In one aspect, the first bottoms comprises less than 0.1 wt. % weight formic ester of the alcohol. In other examples, the first bottoms comprises less than 500 ppm or 200 ppm formate ester of the alcohol.

The operating conditions of the first distillation column are selected based on economic trade-offs with the constraint that formic acid tends to decompose at temperatures greater than about 150° C., with the rate increasing steadily as 150° C. is exceeded. In one aspect, the first distillation column has a base temperature ranging from 80° C. to 165° C. Other examples of the base temperature range include from 90° C. to 158° C. and 100° C. to 157° C. In one aspect, the operating pressure of the first distillation column ranges from 1 bara to 6 bara. Other examples of the operating pressure range include 2 bara to 5 bara and 2 bara to 4.5 bara.

In one aspect, the first distillation column does not comprise a heterogeneous hydrolysis catalyst.

When only compositions approaching the formic acid/water azeotrope are required, the distillation zone may consist of one distillation column. In other aspects, particularly when compositions above 90 wt. % formic acid are required for the formic acid product, a second distillation column is useful.

In one aspect, the distillation zone comprises a second distillation column and the process further comprises feeding the first bottoms to the second distillation column and removing the formic acid product as a second distillate and a second bottoms. Optionally, additional formic acid product concentrations may be obtained by removing sidedraw streams from the second column at concentrations intermediate between the second distillate formic acid concentration and the second bottoms concentration. The second bottoms comprises formic acid in an amount within 7 weight percentage points an amount of formic acid in a formic acid/water azeotrope an operating pressure of the second distillation column. In other examples, the second bottoms comprises formic acid in the amount within 6.5 weight percentage points, 5.5 weight percentage points, or 5.0 weight percentage points of the amount of formic acid in the formic acid/water azeotrope at the operating pressure of the second distillation column. The process further comprises feeding the second bottoms to the first distillation column for further formic acid recovery and water removal. In another aspect, additional formic acid product streams may be created by blending higher and lower product concentration streams.

Feeding the first bottoms to the second distillation column encompasses feeding any amount of the first bottoms, up to and including feeding all of the first bottoms to the second distillation column. In one aspect, the amount of the first bottoms fed to the second distillation column is varied depending upon the demand for relatively low purity formic acid (i.e., 75 wt. %-84 wt. %) as compared to relatively high purity formic acid (i.e., >94 wt. %).

The operating conditions of the second distillation column are selected based on economic trade-offs. In one aspect, the second distillation column has a base temperature ranging from 35° C. to 115° C. Other examples of the base temperature range include from 45° C. to 90° C. and 45° C. to 80° C. In one aspect, the operating pressure of the second distillation column ranges from 0.04 bara to 1.5 bara. Other examples of the operating pressure range include 0.05 bara to 1 bara and 0.06 bara to 0.7 bara.

In one aspect, the operating pressure of the first distillation column and the operating pressure of the second distillation column are set whereby the amount of formic acid in the formic acid/water azeotrope in the first distillation column is at least 10 weight percentage points higher than the amount of formic acid in the formic acid/water azeotrope in the second distillation column. In other examples, the amount of formic acid in the formic acid/water azeotrope in the first distillation column is at least 9 weight percentage points, 7 weight percentage points, or 5 weight percentage points higher than the amount of formic acid in the formic acid/water azeotrope in the second distillation column.

The first distillation column can be operated continuously, semi-continuously, or batch wise as these terms are defined above. The manner in which the formate ester mixture, hydrolysis effluent, and/or water are fed to the first distillation column is not particularly limited. The second distillation column can be operated continuously, semi-continuously, or batch wise as these terms are defined above.

Each distillation column comprises a reboiler, a condenser, and at least one stage. The type of reboiler and condenser is not limited and many types are known to those skilled in the art. In one aspect, the first distillation column comprises 30 to 100 theoretical stages. In one aspect, the second distillation column comprises 25 to 80 theoretical stages.

In one aspect, the process further comprises removing a recycle stream comprising water from the distillation zone and feeding a recycle stream to the hydrolysis zone. In a non-limiting example, the condensate of the vapor leaving the first distillation column forms two liquid phases and a portion of the aqueous phase is recycled to the hydrolysis zone.

In the present embodiment, the process comprises feeding the wet alcohol mixture to an alcohol recovery zone and removing a dry alcohol stream and the hydrolysis recycle stream. The dry alcohol stream comprises the alcohol and less than 1 wt. % water. The hydrolysis recycle stream comprises water, the formate ester of the alcohol, and/or the alcohol. The process comprises feeding the hydrolysis recycle stream to the hydrolysis zone. In other examples, the dry alcohol stream comprises less than 0.5 wt. %, 0.25 wt. %, 0.1 wt. %, 500 ppm, or 200 ppm water.

In one aspect, the alcohol recovery zone comprises processes selected from the group consisting of 1) azeotropic distillation wherein, when the alcohol is a $C_3$ alcohol, the azeotroping agent comprises the formate ester of the alcohol and/or an ether of the alcohol, and when the alcohol is a $C_4$ alcohol, the azeotroping agent comprises the formate ester of the alcohol, the ether of the alcohol, and/or the alcohol; 2) azeotropic distillation using an azeotrope agent comprising $C_5$-$C_6$ hydrocarbons, $C_1$-$C_3$ chlorinated hydrocarbons, and/or $C_4$-$C_8$ ethers; and 3) extractive distillation using an extractant comprising $C_2$-$C_4$ glycols and/or $C_4$-$C_6$ glycol ethers. In one aspect, water is removed overhead as a heterogeneous azeotrope with one or more azeotrope agents, wherein a water-rich phase and an azeotrope agent-rich phase is removed in a decantation step. Both phases may be refluxed as needed to ensure stable operation of the first distillation column. In another aspect, the azeotrope agent is selected from one or more of 2-butanol, 2-butyl formate, and/or di-2-butyl ether.

In one aspect, the overall conversion of formate ester of the alcohol in the formate ester mixture to formic acid in the formic acid product ranges from 10% to 90%. Other examples of the overall conversion ranges are 10% to 75%, 20% to 80%, and 20% to 60%. One skilled in the art will recognize that when the formic acid product consists of the second distillate (i.e., no formic acid products with lower concentrations are removed from the process) the overall conversion is calculated directly using the amount of formic acid in the second distillate. When multiple formic acid products with different formic acid concentrations are removed from the process, the overall conversion will take into account the sum of the moles of formic acid removed in each formic acid product stream.

In one aspect, the hydrolysis reaction also occurs in the distillation zone. In other words, reaction and separation occur simultaneously in at least part of the distillation zone. In one aspect, the formate ester of the alcohol further hydrolyzes in the distillation zone. In one aspect, the overall conversion of formate ester of the alcohol in the formate ester mixture to formic acid in the formic acid product is up to 40 percentage points higher than the hydrolysis conversion. For example, if the overall conversion is 85% and the overall conversion is 40 percentage points higher than the hydrolysis conversion, then the conversion in hydrolysis is 45% (85%—40 percentage points) and the distillation conversion is 40%. In other examples, the overall conversion of formate ester of the alcohol is up to 35 percentage points, 25 percentage point, 10 percentage points, or 5 percentage points higher than the hydrolysis conversion. In one aspect, the overall conversion is substantially the same as the hydrolysis conversion. The overall conversation and hydrolysis conversion are substantially the same when they are within 1.0 percent point of each other.

The feature of substantially the same or increased conversion of formate ester of the alcohol to formic acid in the distillation zone of the present invention is significant in comparison to the production of formic acid from the carbonylation of methanol to methyl formate. In this common industrial process, conversion can actually decrease in the distillation zone. In other words, some of the formic acid fed to the distillation zone actually reacts with methanol to produce methyl formate: the overall conversion is lower than the hydrolysis conversion.

Energy integration can be a key factor in making the separation of formic acid from a formate ester mixture economically viable. In one aspect, the alcohol is selected from the group consisting of iso-propanol and 2-butanol and the process further comprises using energy of condensing a first distillation column vapor to provide heat to one or more of the group consisting of the hydrolysis zone, the alcohol recovery zone, and the second distillation column. In one aspect, the heat is provided directly by condensation of the first distillation column vapor against process fluids. In one aspect, the heat is provided indirectly by generation of steam from condensation of the first distillation column vapor, followed by the use of the steam. A non-limiting example of providing heat directly is using the heat of condensation of the first distillation column vapor on the shell side of the second distillation column reboiler instead of steam. A non-limiting example of providing heat indirectly is using the heat of condensation of the first distillation column vapor to generate steam and using the generated steam to heat the hydrolysis zone.

In another embodiment, a process for producing formic acid comprises feeding carbon monoxide, a fresh feed, and a catalyst feed, to a carbonylation zone. The fresh feed comprises an alcohol and the catalyst feed comprises a homogeneous catalyst. The process comprises carbonylating the alcohol to produce a formate ester of the alcohol, and removing a carbonylation effluent. The carbonylation effluent comprises the formate ester of the alcohol, the alcohol, and the homogeneous catalyst. The process further comprises feeding the carbonylation effluent to a catalyst separation zone and removing a catalyst mixture and a formate ester mixture. The catalyst mixture comprises the homogeneous catalyst and the alcohol and the formate ester mixture comprises the formate ester of the alcohol. The process further comprises feeding the formate ester mixture, a hydrolysis recycle, and water to a hydrolysis zone, hydrolyzing the formate ester of the alcohol, and removing a hydrolysis effluent. The hydrolysis effluent comprises the formate ester of the alcohol, formic acid, and the alcohol. The process further comprises feeding the hydrolysis effluent to a distillation zone and removing a formic acid product and a wet alcohol mixture. The formic acid product comprises greater than 75 wt. % formic acid and the wet alcohol mixture comprises the alcohol, water, the formate ester of the alcohol, and less than 0.5 wt. % formic acid. The process further comprises feeding the wet alcohol mixture to an alcohol recovery zone and removing a dry alcohol stream and a hydrolysis recycle stream. The dry alcohol stream comprises the alcohol and less than 1 wt. % water. The hydrolysis recycle stream comprises water, the formate ester of the alcohol, and/or the alcohol. The alcohol is selected from the group consisting of $C_3$ to $C_4$ alcohols.

The various aspects of the amount of formate ester of the alcohol in the formate ester mixture; the selection of the alcohol; feeding the formate ester mixture, hydrolysis recycle and water to the hydrolysis zone; the molar ratio of water:formate ester of the alcohol; the operating temperature and pressure of the hydrolysis zone; the composition of the formic acid product; the composition of the wet alcohol mixture; the composition of the dry alcohol stream; the distillation zone comprising one or two distillation columns; the first bottoms composition and the second bottoms compositions, the relative operating pressures of the first distillation column and the second distillation column, the first and second distillation column base temperature, operating pressure, and number of theoretical stages; and the overall conversion, hydrolysis conversion, and distillation conversion of formate ester of the alcohol to formic acid; and the heat integration of the previous embodiment apply to this embodiment as well.

The process of the present embodiment comprises feeding carbon monoxide, a fresh feed, and a catalyst feed to a carbonylation zone. The fresh feed comprises an alcohol and the catalyst feed comprises a homogeneous catalyst. The process comprises carbonylating the alcohol to produce a formate ester of the alcohol and removing a carbonylation effluent. The carbonylation effluent comprises the formate ester of the alcohol, the alcohol, and the homogeneous catalyst.

The carbonylation process for carbonylating methanol to produce methyl formate is well known and is described in Ullmann's Encyclopedia of Industrial Chemistry (Reutemann, W.; Kieczka, H., "Formic Acid", Volume 16, 2012, Wiley-VCH Verlag GmbH & Co. KGaA, Weinheim, pp. 13-33), the entirety of which is incorporated herein by reference. In one aspect, the carbonylation zone is operated under conditions similar to those for carbonylating methanol when carbonylating the alcohols of the present invention.

The carbonylation reaction is equilibrium-limited, both by carbon monoxide partial pressure and reaction temperature. Low temperature gives higher equilibrium conversion, but requires long residence times. Higher equilibrium conversion is favored by high carbon monoxide partial pressure, but requires more energy for compression of carbon monoxide and expensive vessel construction. For example, above 90% conversion of 2-butanol is achievable at close to room temperature and around 20-40 bara CO pressure, but a reaction time around 12 hours is needed to reach equilibrium conversion, depending upon catalyst concentration. Thus, tradeoffs are required for economical production of formate esters via carbonylation of the alcohols. The carbonylation is typically carried out at a total pressure (comprising carbon monoxide, alcohol, and formate ester partial pressures at reaction temperature) of 15 to 150 bara, more typically 20 to 80 bara. Temperature of the carbonylation zone may be 20° C. to 140° C., more typically 40° C. to 110° C. The carbonylation is typically carried out with the use of a homogeneous basic catalyst, although use of heterogeneous basic catalysts is known in the art (see for example, Di Girolamo, M.; Marchionna, M., "Acidic and Basic Ion Exchange Resins for Industrial Applications", Journal of Molecular Catalysis A: Chemical 177 (2001) 33-40). In one aspect, the homogeneous catalyst comprises the potassium, sodium, or cesium salt of the alcohol, i.e., alkali alkoxides. Catalyst concentration may vary widely, ranging from 0.1 to 7 wt. % in the total liquid feed to the carbonylation zone. Potassium alkoxides are preferred, as they offer acceptable tradeoffs between cost, catalytic activity, and solubility in the alcohol. Typical concentrations for potassium salts are 0.1 to 5 wt. %, more typically 0.2 to 1.5 wt. % in the liquid feed(s) to the carbonylation zone. The carbonylation reaction is exothermic and equilibrium conversion is retarded by high temperature. Thus, management of the heat of reaction is important. The heat management may be accomplished by any method known in the art. The reaction may be conducted adiabatically, partially adiabatically, or isothermally, batch or continuously. When run adiabatically or partially adiabatically, the liquid feeds to the carbonylation zone must be sufficiently cool to allow for heat rise due to reaction. Typically, the liquid feeds must be cooled at least 10° C., more typically at least 20° C. below the desired adiabatic outlet temperature. Alternatively, heat may be removed while the reaction is carried out, typically within a heat exchanger of any type known in the art, such as shell and tube exchangers, spiral wound exchangers, plate exchangers, and the like. If the desired reaction temperature is sufficiently high, for example above about 90° C., the heat may be removed by generation of steam or other vapors in a boiler-type heat exchanger. The generated steam or vapors may be used as a heat source in other sections of the formic acid producing process where energy is required. For example, the steam or vapors may be used to drive the distillation column used to recover formic acid generated in the hydrolysis of the formate ester of the carrier alcohol.

The process comprises removing the homogeneous catalyst from the carbonylation effluent prior to hydrolyzing the formate ester of the alcohol. In one aspect, the catalyst separation zone comprises a flash vessel maintained at an operating pressure below the operating pressure of the carbonylation zone. The carbonylation effluent is fed to the flash vessel and a vapor stream leaving the flash vessel is condensed and removed from the catalyst mixture as the formate ester mixture. The catalyst mixture, comprising the homogeneous catalyst and the alcohol, leaves the bottom of the flash vessel. In one aspect, essentially all of the homogeneous catalyst leaves the catalyst separation zone in the catalyst mixture. In one aspect, the carbonylation effluent is fed to a distillation column to enrich the amount of formate ester of the alcohol in the formate ester mixture. In the case of an alkali alkoxide catalyst, the alkali alkoxide catalyst is still active for decomposition of the formate ester into carbon monoxide and alcohol. To minimize such decomposition of the formate ester of the alcohol, the distillation column may be operated with low residence time and low temperature. Residence time may be limited by use of packing instead of stages in the section of the column where catalyst and formate ester of the alcohol are in contact, i.e., below the feed point to the column. Residence time may also be limited by designing the reboiler with low residence time in accordance with known methods in the art, i.e., not a kettle-type reboiler, but rather low residence time thermosyphon, falling film, or wiped film reboiler designs. In one aspect, the distillation column is operated with temperatures below about 100° C. or below about 85° C. where the homogeneous catalyst and formate ester of the alcohol are in contact. In one aspect, the distillation column operating pressure is less than 1.5 bara or ranges from 1 to 0.04 bara.

In one aspect, the catalyst feed comprises the catalyst mixture.

In one aspect, the alcohol is selected from the group consisting of iso-propanol, 2-butanol, and tert-butanol and a molar ratio of water:formate ester of the alcohol fed to the hydrolysis zone ranges from 0.5:1 to 3:1, and the hydrolysis zone operates at a temperature from 40° C. to 140° C. and at a pressure from 1 bara to 40 bara.

In one aspect, the distillation zone comprises a first distillation column and a second distillation column. The process further comprises b1) feeding the hydrolysis effluent to the first distillation column and removing the wet alcohol mixture as a first distillate, and a first bottoms. The first bottoms comprises formic acid in an amount within 9 weight percentage points of an amount of formic acid in a formic acid/water azeotrope at an operating pressure of the first distillation column. The process also comprises, b2) feeding the first bottoms to a second distillation column and removing the formic acid product as a second distillate, and a second bottoms. The second bottoms comprises formic acid in an amount within 7 weight percentage points of an amount of formic acid in a formic acid/water azeotrope at an operating pressure of the second distillation column. The process also comprises b3) feeding the second bottoms to the first distillation column.

In one aspect, the alcohol recover zone comprises a process selected from the group consisting of c1) azeotropic distillation wherein; when the alcohol is a $C_3$ alcohol, the azeotroping agent comprises the formate ester of the alcohol and/or an ether of the alcohol; and when the alcohol is a $C_4$ alcohol, the azeotroping agent comprises the formate ester of the alcohol, the ether of the alcohol, and/or the alcohol; c2) azeotropic distillation using an azeotrope agent comprising $C_5$-$C_6$ hydrocarbons, $C_1$-$C_3$ chlorinated hydrocarbons, and/or $C_4$-$C_8$ ethers; and c3) extractive distillation using an extractant comprising $C_2$-$C_4$ glycols and/or $C_4$-$C_6$ glycol ethers.

In yet another embodiment, a process for producing formic acid comprises feeding methanol, a dry alcohol stream, and a catalyst recycle to a dehydrogenative coupling (DHC) zone. The dry alcohol stream comprises the alcohol and less than 1 wt. % water. The process comprises performing a DHC reaction of methanol with the alcohol to produce a formate ester of the alcohol and hydrogen, and removing a DHC effluent. The DHC effluent comprises the formate ester of the alcohol and a homogeneous catalyst. The process further comprises feeding the DHC effluent to a catalyst separation zone and removing the catalyst recycle and a formate ester mixture. The catalyst recycle comprises the homogeneous catalyst and the formate ester mixture comprises the formate ester of the alcohol. The process further comprises feeding the formate ester mixture, a hydrolysis recycle, and water to a hydrolysis zone, hydrolyzing the formate ester of the alcohol, and removing a hydrolysis effluent. The hydrolysis effluent comprises the formate ester of the alcohol, formic acid, and the alcohol. The process further comprises feeding the hydrolysis effluent to a distillation zone and removing a formic acid product and a wet alcohol mixture. The formic acid product comprises greater than 75 wt. % formic acid, and the wet alcohol mixture comprises the alcohol, water, the formate ester of the alcohol, and less than 0.5 wt. % formic acid. The process further comprises feeding the wet alcohol mixture to an alcohol recovery zone and removing a dry alcohol stream and the hydrolysis recycle. The hydrolysis recycle comprises water, the formate ester of the alcohol, and/or the alcohol. The alcohol is selected from the group consisting of iso-propanol, 2-butanol, and tert-butanol.

The various aspects of the amount of formate ester of the alcohol in the formate ester mixture; the selection of the alcohol; feeding the formate ester mixture, hydrolysis recycle and water to the hydrolysis zone; the molar ratio of water:formate ester of the alcohol; the operating temperature and pressure of the hydrolysis zone; the composition of the formic acid product; the composition of the wet alcohol mixture; the composition of the dry alcohol stream; the distillation zone comprising one or two distillation columns; the first bottoms composition and the second bottoms compositions, the relative operating pressures of the first distillation column and the second distillation column, the first and second distillation column base temperature, operating pressure, and number of theoretical stages; and the overall conversion, hydrolysis conversion, and distillation conversion of formate ester of the alcohol to formic acid, and the heat integration of the previous embodiment apply to this embodiment as well.

In one aspect, the alcohol is selected from the group consisting of iso-propanol and 2-butanol. In one aspect, the alcohol is iso-propanol. In one aspect, the alcohol is 2-butanol. In one aspect, the alcohol is tert-butanol.

In the present embodiment, a process for producing formic acid comprises feeding methanol, a dry alcohol stream, and a catalyst recycle to a dehydrogenative coupling (DHC) zone. The dry alcohol stream comprises the alcohol and less than 1 wt. % water. The process comprises performing a DHC reaction of methanol with the alcohol to produce a formate ester of the alcohol and hydrogen, and removing a DHC effluent. The process of preparing a formate ester of the alcohol by contacting methanol with the alcohol in the presence of an iron-based catalyst is described in detail in U.S. Application No. 62/540,317, filed on the same day as the present application, the content of which is hereby incorporated by reference in its entirety.

In one aspect, the catalyst or catalyst precursor(s) is/are combined with methanol and an alcohol selected from the group consisting of iso-propanol, 2-butanol, and tert-butanol, and optionally a solvent and/or a hydrogen acceptor, at a catalyst-to-methanol weight ratio of 1:10 to 1:100,000 in a reactor. The mixture is heated with mixing to a temperature of 40 to 160° C. for a period of 1-6 hours during which time hydrogen ($H_2$) may evolve, and hydrogen may be removed from the reactor. It is possible to carry the reaction to full conversion, but it may be advantageous to limit the conversion due to rates and reaction pressures.

The process comprises removing the homogeneous catalyst from the DHC effluent prior to hydrolyzing the formate ester of the alcohol. In one aspect, the catalyst separation zone comprises a flash vessel maintained at an operating pressure below the operating pressure of the DHC zone. The DHC effluent is fed to the flash vessel and a vapor stream leaving the flash vessel is condensed and removed from the catalyst separation zone as the formate ester mixture. The catalyst recycle, comprising the homogeneous catalyst, leaves the bottom of the flash vessel. In one aspect, essentially all of the homogeneous catalyst leaves the catalyst separation zone in the catalyst recycle. In one aspect, the DHC effluent is fed to a distillation column to enrich the amount of formate ester of the alcohol in the formate ester mixture. The distillation column is operated with temperatures below about 170° C. or about 110° C. where catalyst and formate ester of the alcohol are stable The distillation column is operated at pressures less than 3 bara or ranging from 1.5 to 0.04 bara. In another aspect, the homogeneous catalyst is concentrated in the retentate of a membrane permeation process, and the permeate comprises the formate ester mixture.

In one aspect, the distillation zone comprises a first distillation column and a second distillation column. The process further comprises b1) feeding the hydrolysis effluent to the first distillation column and removing the wet alcohol mixture as a first distillate, and a first bottoms. The first bottoms comprises formic acid in an amount within 9 weight percentage points of an amount of formic acid in a formic acid/water azeotrope at an operating pressure of the first distillation column. The process also comprises, b2) feeding the first bottoms to a second distillation column and removing the formic acid product as a second distillate, and a second bottoms. The second bottoms comprises formic acid in an amount within 7 weight percentage points of an amount of formic acid in a formic acid/water azeotrope at an operating pressure of the second distillation column. The process also comprises b3) feeding the second bottoms to the first distillation column.

In one aspect, the alcohol recover zone comprises a process selected from the group consisting of c1) azeotropic distillation wherein; when the alcohol is a $C_3$ alcohol, the azeotroping agent comprises the formate ester of the alcohol and/or an ether of the alcohol; and when the alcohol is a $C_4$ alcohol, the azeotroping agent comprises the formate ester of the alcohol, the ether of the alcohol, and/or the alcohol; c2) azeotropic distillation using an azeotrope agent comprising $C_5$-$C_6$ hydrocarbons, $C_1$-$C_3$ chlorinated hydrocarbons, and/or $C_4$-$C_8$ ethers; and c3) extractive distillation using an extractant comprising $C_2$-$C_4$ glycols and/or $C_4$-$C_6$ glycol ethers.

Listed below are non-limiting embodiments A1-A26.

A1. A process for recovering formic acid from a formate ester mixture, wherein the process comprises,
    a) feeding the formate ester mixture, a hydrolysis recycle, and water to a hydrolysis zone, wherein the formate esters mixture comprises a formate ester of an alcohol, hydrolyzing the formate ester of the alcohol, and removing a hydrolysis effluent comprising the formate ester of the alcohol, formic acid, and the alcohol;
    b) feeding the hydrolysis effluent to a distillation zone and removing a formic acid product and a wet alcohol mixture, wherein the formic acid product comprises greater than 75 wt. % formic acid and the wet alcohol mixture comprises the alcohol, water, the formate ester of the alcohol, and less than 0.5 wt. % formic acid; and
    c) feeding the wet alcohol mixture to an alcohol recovery zone and removing a dry alcohol stream and the hydrolysis recycle, wherein the dry alcohol stream comprises the alcohol and less than 1 wt. % water, and the hydrolysis recycle stream comprises water, the formate ester of the alcohol, and/or the alcohol,
wherein the alcohol is selected from the group consisting of $C_3$ to $C_4$ alcohols.

A2. The process of embodiment A1, wherein the formate ester mixture comprises at least 10 wt. %, 20 wt. %, 25 wt. %, 45 wt. %, 50 wt. %, 75 wt. %, or 90 wt. % formate ester of the alcohol.

A3. The process of any of embodiments A1-A2, wherein the alcohol is selected from the group consisting of n-propanol, iso-propanol, n-butanol, iso-butanol, 2-butanol, and tert-butanol; or the alcohol is selected from the group consisting of iso-propanol, 2-butanol, and tert-butanol; or the alcohol is selected from the group consisting of iso-propanol and 2-butanol; or the alcohol is iso-propanol; or the alcohol is 2-butanol.

A4. The process of any of embodiments A1-A3, wherein a molar ratio of water:formate ester of the alcohol fed to the hydrolysis zone ranges from 0.5:1 to 3:1, or 0.8: to 2.4:1, or 1.2:1 to 2:1.

A5. The process of any of embodiments A1-A4, wherein the hydrolysis zone operates at a temperature from 40° C. to 140° C. and at a pressure from 1 bara to 40 bara.

A6. The process of any of embodiments A1-A5, wherein the formic acid product comprises greater than 75 wt. %, 78 wt. %, 80 wt. %, 82 wt. %, 90 wt. %, 94 wt. %, 95 wt. %, 97 wt. % or 99 wt. % formic acid.

A7. The process of any of embodiments A1-A6, wherein the wet alcohol mixture comprises less than 0.1 wt. %, 500 ppm, or 200 ppm formic acid.

A8. The process of any of embodiments A1-A7, wherein the dry alcohol stream comprises less than 0.5 wt. %, 0.25 wt. %, 0.1 wt. %, 500 ppm, or 200 ppm water.

A9. The process of any of embodiments A1-A8, wherein an overall conversion of the formate ester of the alcohol in the formate ester mixture ranges from 10% to 90%, 10% to 75%, or 20% to 60%.

A10. The process of any of embodiments A1-A9, wherein an overall conversion of the formate ester of the alcohol in the formate ester mixture is up to 40 percentage points, 35 percentage points, 25 percentage point, or 10 percentage points higher than the hydrolysis conversion of the formate ester of the alcohol.

A11. The process of any of embodiments A1-A10, wherein the distillation zone comprises a first distillation column, wherein the process further comprises
    b1) feeding the hydrolysis effluent to the first distillation column and removing the wet alcohol mixture as a first distillate and a first bottoms comprising formic acid in an amount within 9 weight percentage points of an amount of formic acid in a formic acid/water azeotrope at an operating pressure of the first distillation column.

A12. The process of embodiment A11, wherein the first bottoms comprises less than 0.1 wt. %, 500 ppm, or 200 ppm formate ester of the alcohol.

A13. The process of any of embodiments A11-A12, wherein the first bottoms comprises formic acid in the amount within 7.5 weight percentage points, 7.0 weight percentage points, or 5.0 weight percentage points of the amount of formic acid in the formic acid/water azeotrope at the operating pressure of the first distillation column.

A14. The process of any of embodiments A11-A13, with the proviso that the first distillation column does not comprise a heterogeneous hydrolysis catalyst.

A15. The process of any of embodiments A11-A14, wherein the first distillation column has a base temperature ranging from 80° C. to 165° C., 90° C. to 158° C., or 100° C. to 157° C., and the operating pressure of the first distillation ranges from 1 bara to 6 bara, 2 bara to 5 bara, or 2 bara to 4.5 bara.

A16. The process of any of embodiments A11-A15, wherein the first distillation column comprises 30 to 100 theoretical stages.

A17. The process of any of embodiments A11-A16, wherein the formic acid product comprises the first bottoms.

A18. The process of any of embodiments A11-A16, wherein the distillation zone further comprises a second distillation column, wherein the process further comprises
b2) feeding the first bottoms to the second distillation column and removing the formic acid product as a second distillate and a second bottoms comprising formic acid in an amount within 7 weight percentage points of an amount of formic acid in a formic acid/water azeotrope at an operating pressure of the second distillation column; and
b3) feeding the second bottoms to the first distillation column.

A19. The process of embodiment A18, wherein the operating pressure of the first distillation column and the operating pressure of the second distillation column are set whereby the amount of formic acid in the formic acid/water azeotrope in the first distillation column is at least 10 weight percentage points higher than the amount of formic acid in the formic acid/water azeotrope in the second distillation column.

A20. The process of any of embodiments A18-A19, wherein the second bottoms comprises formic acid in the amount within 6.5 weight percentage points, 5.5 weight percentage points, or 5.0 weight percentage points of the amount of formic acid in the formic acid/water azeotrope at the operating pressure of the second distillation column.

A21. The process of any of embodiments A18-A20, wherein the second distillation column comprises 25 to 80 theoretical stages.

A22. The process of any of embodiments A1-A21, wherein the alcohol recovery zone comprises a process selected from the group consisting of
c1) azeotropic distillation wherein; when the alcohol is a $C_3$ alcohol, the azeotroping agent comprises the formate ester of the alcohol and/or an ether of the alcohol; and when the alcohol is a $C_4$ alcohol, the azeotroping agent comprises the formate ester of the alcohol, the ether of the alcohol, and/or the alcohol;
c2) azeotropic distillation using an azeotrope agent comprising $C_5$-$C_6$ hydrocarbons, $C_1$-$C_3$ chlorinated hydrocarbons, and/or $C_4$-$C_8$ ethers; and
c3) extractive distillation using an extractant comprising $C_2$-$C_4$ glycols and/or $C_4$-$C_6$ glycol ethers.

A23. The process of any of embodiments A18-A22, wherein the alcohol is selected from the group consisting of iso-propanol and 2-butanol, further comprising using energy of condensing a first distillation column vapor to provide heat to one or more of the group consisting of the hydrolysis zone, the alcohol recovery zone, and the second distillation column.

A24. The process of embodiment A23, wherein the heat is provided directly by condensation of the first distillation column vapor against process fluids and/or wherein the heat is provided indirectly by generation of steam from condensation of the first distillation column vapor, followed by the use of the steam.

A25. The process of any of embodiments A1-A21, further comprising
e) feeding carbon monoxide, a fresh feed, and a catalyst feed, to a carbonylation zone, wherein the fresh feed comprises the alcohol and the catalyst feed comprises a homogeneous catalyst, carbonylating the alcohol to produce the formate ester of the alcohol, and removing a carbonylation effluent comprising the formate ester of the alcohol, the alcohol, and the homogeneous catalyst; and
f) feeding the carbonylation effluent to a catalyst separation zone and removing a catalyst mixture and the formate ester mixture, wherein the catalyst mixture comprises the homogeneous catalyst and the alcohol.

A26. The process of any of embodiments A1-A24, wherein the alcohol is selected from the group consisting of iso-propanol, 2-butanol, and tert-butanol, and the process further comprises
e) feeding methanol, a dry alcohol stream, and a catalyst recycle to a dehydrogenative coupling (DHC) zone, performing a DHC reaction of methanol with the alcohol to produce a formate ester of the alcohol and hydrogen, and removing a DHC effluent comprising the formate ester of the alcohol and a homogeneous catalyst; and
f) feeding the DHC effluent to a catalyst separation zone and removing the catalyst recycle and the formate ester mixture, wherein the catalyst recycle comprises the homogeneous catalyst.

Listed below are non-limiting embodiments B1-B26.

B1. A process for producing formic acid, wherein the process comprises,
a) feeding carbon monoxide, a fresh feed, and a catalyst feed, to a carbonylation zone, wherein the fresh feed comprises an alcohol and the catalyst feed comprises a homogeneous catalyst, carbonylating the alcohol to produce a formate ester of the alcohol, and removing a carbonylation effluent comprising the formate ester of the alcohol, the alcohol, and the homogeneous catalyst;
b) feeding the carbonylation effluent to a catalyst separation zone and removing a catalyst mixture and a formate ester mixture, wherein the catalyst mixture comprises the homogeneous catalyst and the alcohol, and the formate ester mixture comprises the formate ester of the alcohol;
c) feeding the formate ester mixture, a hydrolysis recycle, and water to a hydrolysis zone, hydrolyzing the formate ester of the alcohol, and removing a hydrolysis effluent comprising the formate ester of the alcohol, formic acid, and the alcohol;

d) feeding the hydrolysis effluent to a distillation zone and removing a formic acid product and a wet alcohol mixture, wherein the formic acid product comprises greater than 75 wt. % formic acid and the wet alcohol mixture comprises the alcohol, water, the formate ester of the alcohol, and less than 0.5 wt. % formic acid; and e) feeding the wet alcohol mixture to an alcohol recovery zone and removing a dry alcohol stream and the hydrolysis recycle, wherein the dry alcohol stream comprises the alcohol and less than 1 wt. % water, and the hydrolysis recycle comprises water, the formate ester of the alcohol, and/or the alcohol, wherein the alcohol is selected from the group consisting of $C_3$ to $C_4$ alcohols.

B2. The process of embodiment B1, wherein the formate ester mixture comprises at least 10 wt. %, 20 wt. %, 25 wt. %, 45 wt. %, 50 wt. %, 75 wt. %, or 90 wt. % formate ester of the alcohol.

B3. The process of any of embodiments B1-B2, wherein the alcohol is selected from the group consisting of n-propanol, iso-propanol, n-butanol, iso-butanol, 2-butanol, and tert-butanol; or the alcohol is selected from the group consisting of iso-propanol, 2-butanol, and tert-butanol; or the alcohol is selected from the group consisting of iso-propanol and 2-butanol; or the alcohol is iso-propanol; or the alcohol is 2-butanol.

B4. The process of any of embodiments B1-B3, wherein a molar ratio of water:formate ester of the alcohol fed to the hydrolysis zone ranges from 0.5:1 to 3:1, or 0.8: to 2.4:1, or 1.2:1 to 2:1.

B5. The process of any of embodiments B1-B4, wherein the hydrolysis zone operates at a temperature from 40° C. to 140° C. and at a pressure from 1 bara to 40 bara.

B6. The process of any of embodiments B1-B5, wherein the formic acid product comprises greater than 75 wt. %, 78 wt. %, 80 wt. %, 82 wt. %, 90 wt. %, 94 wt. %, 95 wt. %, 97 wt. % or 99 wt. % formic acid.

B7. The process of any of embodiments B1-B6, wherein the wet alcohol mixture comprises less than 0.1 wt. %, 500 ppm, or 200 ppm formic acid.

B8. The process of any of embodiments B1-B7, wherein the dry alcohol stream comprises less than 0.5 wt. %, 0.25 wt. %, 0.1 wt. %, 500 ppm, or 200 ppm water.

B9. The process of any of embodiments B1-B8, wherein an overall conversion of the formate ester of the alcohol in the formate ester mixture ranges from 10% to 90%, 10% to 75%, or 20% to 60%.

B10. The process of any of embodiments B1-B9, wherein an overall conversion of the formate ester of the alcohol in the formate ester mixture is up to 40 percentage points, 35 percentage points, 25 percentage point, or 10 percentage points higher than the hydrolysis conversion of the formate ester of the alcohol.

B11. The process of any of embodiments B1-B10, wherein the distillation zone comprises a first distillation column, wherein the process further comprises b1) feeding the hydrolysis effluent to the first distillation column and removing the wet alcohol mixture as a first distillate and a first bottoms comprising formic acid in an amount within 9 weight percentage points of an amount of formic acid in a formic acid/water azeotrope at an operating pressure of the first distillation column.

B12. The process of embodiment B11, wherein the first bottoms comprises less than 0.1 wt. %, 500 ppm, or 200 ppm formate ester of the alcohol.

B13. The process of any of embodiments B11-B12, wherein the first bottoms comprises formic acid in the amount within 7.5 weight percentage points, 7.0 weight percentage points, or 5.0 weight percentage points of the amount of formic acid in the formic acid/water azeotrope at the operating pressure of the first distillation column.

B14. The process of any of embodiments B11-B13, with the proviso that the first distillation column does not comprise a heterogeneous hydrolysis catalyst.

B15. The process of any of embodiments B11-B14, wherein the first distillation column has a base temperature ranging from 80° C. to 165° C., 90° C. to 158° C., or 100° C. to 157° C., and the operating pressure of the first distillation ranges from 1 bara to 6 bara, 2 bara to 5 bara, or 2 bara to 4.5 bara.

B16. The process of any of embodiments B11-B15, wherein the first distillation column comprises 30 to 100 theoretical stages.

B17. The process of any of embodiments B11-B16, wherein the formic acid product comprises the first bottoms.

B18. The process of any of embodiments B11-B17, wherein the distillation zone further comprises a second distillation column, wherein the process further comprises b2) feeding a portion of the first bottoms to the second distillation column and removing the formic acid product as a second distillate and a second bottoms comprising formic acid in an amount within 7 weight percentage points of an amount of formic acid in a formic acid/water azeotrope at an operating pressure of the second distillation column; and b3) feeding the second bottoms to the first distillation column.

B19. The process of embodiment B18, wherein the operating pressure of the first distillation column and the operating pressure of the second distillation column are set whereby the amount of formic acid in the formic acid/water azeotrope in the first distillation column is at least 10 weight percentage points higher than the amount of formic acid in the formic acid/water azeotrope in the second distillation column.

B20. The process of any of embodiments B18-B19, wherein the second bottoms comprises formic acid in the amount within 6.5 weight percentage points, 5.5 weight percentage points, or 5.0 weight percentage points of the amount of formic acid in the formic acid/water azeotrope at the operating pressure of the second distillation column.

B21. The process of any of embodiments B18-B20, wherein the second distillation column comprises 25 to 80 theoretical stages.

B22. The process of any of embodiments B1-B21, wherein the alcohol recovery zone comprises a process selected from the group consisting of c1) azeotropic distillation wherein; when the alcohol is a $C_3$ alcohol, the azeotroping agent comprises the formate ester of the alcohol and/or an ether of the alcohol; and when the alcohol is a $C_4$ alcohol, the azeotroping agent comprises the formate ester of the alcohol, the ether of the alcohol, and/or the alcohol;

c2) azeotropic distillation using an azeotrope agent comprising $C_5$-$C_6$ hydrocarbons, $C_1$-$C_3$ chlorinated hydrocarbons, and/or $C_4$-$C_8$ ethers; and c3) extractive distillation using an extractant comprising $C_2$-$C_4$ glycols and/or $C_4$-$C_6$ glycol ethers.

B23. The process of any of embodiments B18-B22, wherein the alcohol is selected from the group consisting of iso-propanol and 2-butanol, further comprising using energy of condensing a first distillation column vapor to provide heat to one or more of the group consisting of the hydrolysis zone, the alcohol recovery zone, and the second distillation column.

B24. The process of embodiment B23, wherein the heat is provided directly by condensation of the first distillation column vapor against process fluids and/or wherein the heat is provided indirectly by generation of steam from condensation of the first distillation column vapor, followed by the use of the steam.

B25. The process of any of embodiments B1-B24, wherein the fresh feed comprises the dry alcohol stream.

B26. The process of any of embodiments B1-B25, wherein the catalyst feed comprises the catalyst mixture.

Listed below are non-limiting embodiments C1-C24.

C1. A process for producing formic acid, wherein the process comprises,
  a) feeding methanol, a dry alcohol stream, and a catalyst recycle, to a dehydrogenative coupling (DHC) zone, wherein the dry alcohol stream comprises the alcohol and less than 1 wt. % water, performing a DHC reaction of the methanol and the alcohol to produce a formate ester of the alcohol and hydrogen, and removing a DHC effluent comprising the formate ester of the alcohol, the alcohol, and a homogeneous catalyst;
  b) feeding the DCH effluent to a catalyst separation zone and removing the catalyst recycle and a formate ester mixture, wherein the catalyst recycle comprises the homogeneous catalyst and the alcohol, and the formate ester mixture comprises the formate ester of the alcohol;
  c) feeding the formate ester mixture, a hydrolysis recycle, and water to a hydrolysis zone, hydrolyzing the formate ester of the alcohol, and removing a hydrolysis effluent comprising the formate ester of the alcohol, formic acid, and the alcohol;
  d) feeding the hydrolysis effluent to a distillation zone and removing a formic acid product and a wet alcohol mixture, wherein the formic acid product comprises greater than 75 wt. % formic acid and the wet alcohol mixture comprises the alcohol, water, the formate ester of the alcohol, and less than 0.5 wt. % formic acid; and
  e) feeding the wet alcohol mixture to an alcohol recovery zone and removing the dry alcohol stream and a hydrolysis recycle, wherein the hydrolysis recycle comprises water, the formate ester of the alcohol, and/or the alcohol,
  wherein the alcohol is selected from the group consisting of iso-propanol, 2-butanol, and tert-butanol.

C2. The process of embodiment C1, wherein the formate ester mixture comprises at least 10 wt. %, 20 wt. %, 25 wt. %, 45 wt. %, 50 wt. %, 75 wt. %, or 90 wt. % formate ester of the alcohol.

C3. The process of any of embodiments C1-C2, wherein the alcohol is selected from the group consisting of iso-propanol and 2-butanol; or the alcohol is iso-propanol; or the alcohol is 2-butanol.

C4. The process of any of embodiments C1-C3, wherein a molar ratio of water:formate ester of the alcohol fed to the hydrolysis zone ranges from 0.5:1 to 3:1, or 0.8: to 2.4:1, or 1.2:1 to 2:1.

C5. The process of any of embodiments C1-C4, wherein the hydrolysis zone operates at a temperature from 40° C. to 140° C. and at a pressure from 1 bara to 40 bara.

C6. The process of any of embodiments C1-C5, wherein the formic acid product comprises greater than 75 wt. %, 78 wt. %, 80 wt. %, 82 wt. %, 90 wt. %, 94 wt. %, 95 wt. %, 97 wt. % or 99 wt. % formic acid.

C7. The process of any of embodiments C1-C6, wherein the wet alcohol mixture comprises less than 0.1 wt. %, 500 ppm, or 200 ppm formic acid.

C8. The process of any of embodiments C1-C7, wherein the dry alcohol stream comprises less than 0.5 wt. %, 0.25 wt. %, 0.1 wt. %, 500 ppm, or 200 ppm water.

C9. The process of any of embodiments C1-C8, wherein an overall conversion of the formate ester of the alcohol in the formate ester mixture ranges from 10% to 90%, 10% to 75%, or 20% to 60%.

C10. The process of any of embodiments C1-C9, wherein an overall conversion of the formate ester of the alcohol in the formate ester mixture is up to 40 percentage points, 35 percentage points, 25 percentage point, or 10 percentage points higher than the hydrolysis conversion of the formate ester of the alcohol.

C11. The process of any of embodiments C1-C10, wherein the distillation zone comprises a first distillation column, wherein the process further comprises
  b1) feeding the hydrolysis effluent to the first distillation column and removing the wet alcohol mixture as a first distillate and a first bottoms comprising formic acid in an amount within 9 weight percentage points of an amount of formic acid in a formic acid/water azeotrope at an operating pressure of the first distillation column.

C12. The process of embodiment O11, wherein the first bottoms comprises less than 0.1 wt. %, 500 ppm, or 200 ppm formate ester of the alcohol.

C13. The process of any of embodiments C11-C12, wherein the first bottoms comprises formic acid in the amount within 7.5 weight percentage points, 7.0 weight percentage points, or 5.0 weight percentage points of the amount of formic acid in the formic acid/water azeotrope at the operating pressure of the first distillation column.

C14. The process of any of embodiments C11-C13, with the proviso that the first distillation column does not comprise a heterogeneous hydrolysis catalyst.

C15. The process of any of embodiments C11-C14, wherein the first distillation column has a base temperature ranging from 80° C. to 165° C., 90° C. to 158° C., or 100° C. to 157° C., and the operating pressure of the first distillation ranges from 1 bara to 6 bara, 2 bara to 5 bara, or 2 bara to 4.5 bara.

C16. The process of any of embodiments C11-C15, wherein the first distillation column comprises 30 to 100 theoretical stages.

C17. The process of any of embodiments C11-C16, wherein the formic acid product comprises the first bottoms.

C18. The process of any of embodiments C11-C16, wherein the distillation zone further comprises a second distillation column, wherein the process further comprises
  b2) feeding the first bottoms to the second distillation column and removing the formic acid product as a second distillate and a second bottoms comprising formic acid in an amount within 7 weight percentage points of an amount of formic acid in a formic acid/water azeotrope at an operating pressure of the second distillation column; and
  b3) feeding the second bottoms to the first distillation column.

C19. The process of embodiment C18, wherein the operating pressure of the first distillation column and the operating pressure of the second distillation column are set whereby the amount of formic acid in the formic acid/water azeotrope in the first distillation column is at least 10 weight percentage points higher than the amount of formic acid in the formic acid/water azeotrope in the second distillation column.

C20. The process of any of embodiments C18-C19, wherein the second bottoms comprises formic acid in the amount within 6.5 weight percentage points, 5.5 weight percentage points, or 5.0 weight percentage points of the amount of formic acid in the formic acid/water azeotrope at the operating pressure of the second distillation column.

C21. The process of any of embodiments C18-C20, wherein the second distillation column comprises 25 to 80 theoretical stages.

C22. The process of any of embodiments C1-C21, wherein the alcohol recovery zone comprises processes selected from the group consisting of
- c1) azeotropic distillation wherein; when the alcohol is a $C_3$ alcohol, the azeotroping agent comprises the formate ester of the alcohol and/or an ether of the alcohol; and when the alcohol is a $C_4$ alcohol, the azeotroping agent comprises the formate ester of the alcohol, the ether of the alcohol, and/or the alcohol;
- c2) azeotropic distillation using an azeotrope agent comprising $C_5$-$C_6$ hydrocarbons, $C_1$-$C_3$ chlorinated hydrocarbons, and/or $C_4$-$C_8$ ethers; and
- c3) extractive distillation using an extractant comprising $C_2$-$C_4$ glycols and/or $C_4$-$C_6$ glycol ethers.

C23. The process of any of embodiments C18-C22, wherein the alcohol is selected from the group consisting of iso-propanol and 2-butanol, further comprising using energy of condensing a first distillation column vapor to provide heat to one or more of the group consisting of the hydrolysis zone, the alcohol recovery zone, and the second distillation column.

C24. The process of embodiment C23, wherein the heat is provided directly by condensation of the first distillation column vapor against process fluids and/or wherein the heat is provided indirectly by generation of steam from condensation of the first distillation column vapor, followed by the use of the steam.

FIG. 1 represents a non-limiting embodiment of the present invention. Specifically, FIG. 1 illustrates a non-limiting process flow diagram of the recovery of formic acid from a formate ester mixture.

Formate ester mixture 114 comprises 2-butyl formate and 2-butanol. Formate ester mixture 114 and water 116 are fed to hydrolysis zone 40. Hydrolysis effluent 118 comprises formic acid, 2-butyl formate, 2-butanol, and water and is fed to distillation zone 55. In distillation zone 55, hydrolysis effluent is separated into formic acid product 126 comprising greater than 75 wt. % formic acid, wet alcohol mixture 124 comprising water, 2-butanol, 2-butyl formate and less than 0.5 wt. % formic acid. Wet alcohol mixture 124 is fed to Alcohol recovery zone 85 to produce dry alcohol stream 134 and hydrolysis recycle stream 140. Hydrolysis recycle stream 140 is fed to Hydrolysis zone 40.

Figure 2:
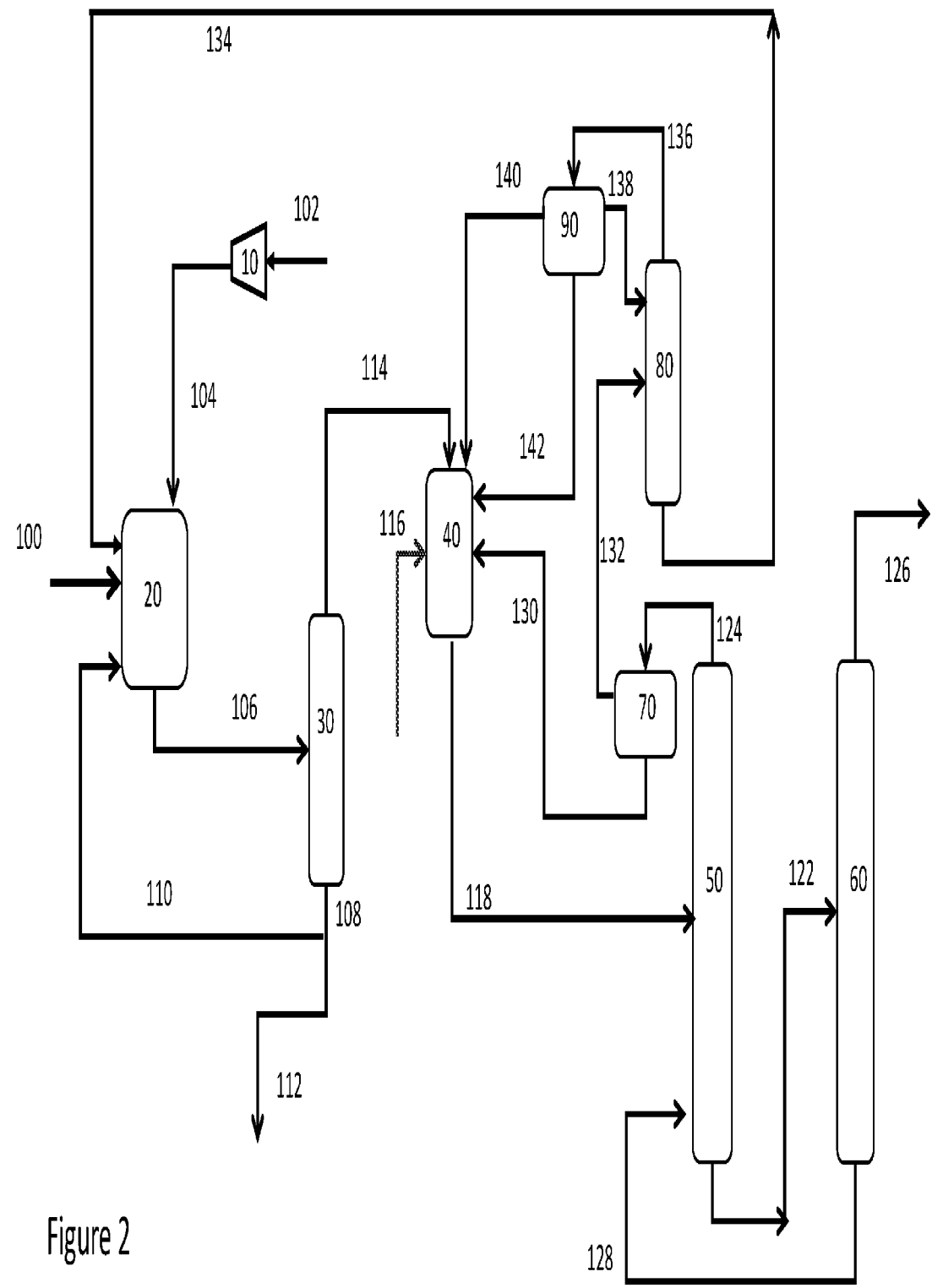
FIG. 2 illustrates a non-limiting process flow diagram of the production of formic acid via carbonylation of 2-butanol.

FIG. 2 illustrates a non-limiting process flow diagram of the production of formic acid via carbonylation of 2-butanol. Fresh 2-butanol 100 is fed to carbonylation reactor 20 along with catalyst feed 110 and dry 2-butanol recycle 134. Carbon monoxide 102 is fed to compressor 10 where it is compressed and pressurized carbon monoxide 104 is fed to carbonylation reactor 20. Carbonylation effluent 106, comprising 2-butanol, 2-butyl formate, and catalyst, exits carbonylation reactor 20 and feeds catalyst separation zone 30. Catalyst mixture 108, comprising 2-butanol and catalyst, is removed from catalyst separation zone 30. Catalyst mixture 108 splits into catalyst feed 110 which is recycled back to carbonylation reactor 20 and purge 112.

Formate ester mixture 114 from catalyst separation zone 30 comprises 2-butyl formate and 2-butanol. Formate ester mixture 114 and water 116 are fed to hydrolysis reactor 40. Hydrolysis effluent 118 comprises formic acid, 2-butyl formate, 2-butanol, and water and is fed to first distillation column 50. First distillation column 50 may be operated at an operating pressure of around 4 bara with a corresponding bottoms temperature around 155° C. and a first bottoms 122 composition close to the formic acid/water azeotrope (about 80 wt. % formic acid/20 wt. % water). First bottoms 122 is fed to second distillation column 60. Second distillation column 60 may be operated at an operating pressure of around 0.1 bara with a corresponding bottoms temperature around 50° C. and a second bottoms 128 composition close to the corresponding formic acid/water azeotrope (about 70 wt. % formic acid/30 wt. % water). Second bottoms 128 is recycled to first distillation column 50. Second distillate 126 comprises formic acid. Typically, second distillate 126 comprises at least 75 wt. % formic acid and can comprise greater than 99 wt. % formic acid.

First vapor 124 is condensed and fed to decanter 70 wherein two phases form. Recycle 130, comprising water, is recycled to hydrolysis reactor 40. Organic stream 132, comprising 2-butyl formate and 2-butanol, is fed to third distillation column 80. Third bottoms 134, comprising dry 2-butanol, is recycled to carbonylation reactor 20. Third vapor 136, comprising 2-butyl formate, 2-butanol, and water is condensed and fed to decanter 90 wherein two phases form. Recycle 142, comprising water, is recycled to hydrolysis reactor 40. Recycle 140, comprising 2-butyl formate and 2-butanol, is also recycled to hydrolysis reactor 40. Reflux 138, comprising 2-butyl formate and 2-butanol is fed to the top of third distillation column 80.

Figure 3:
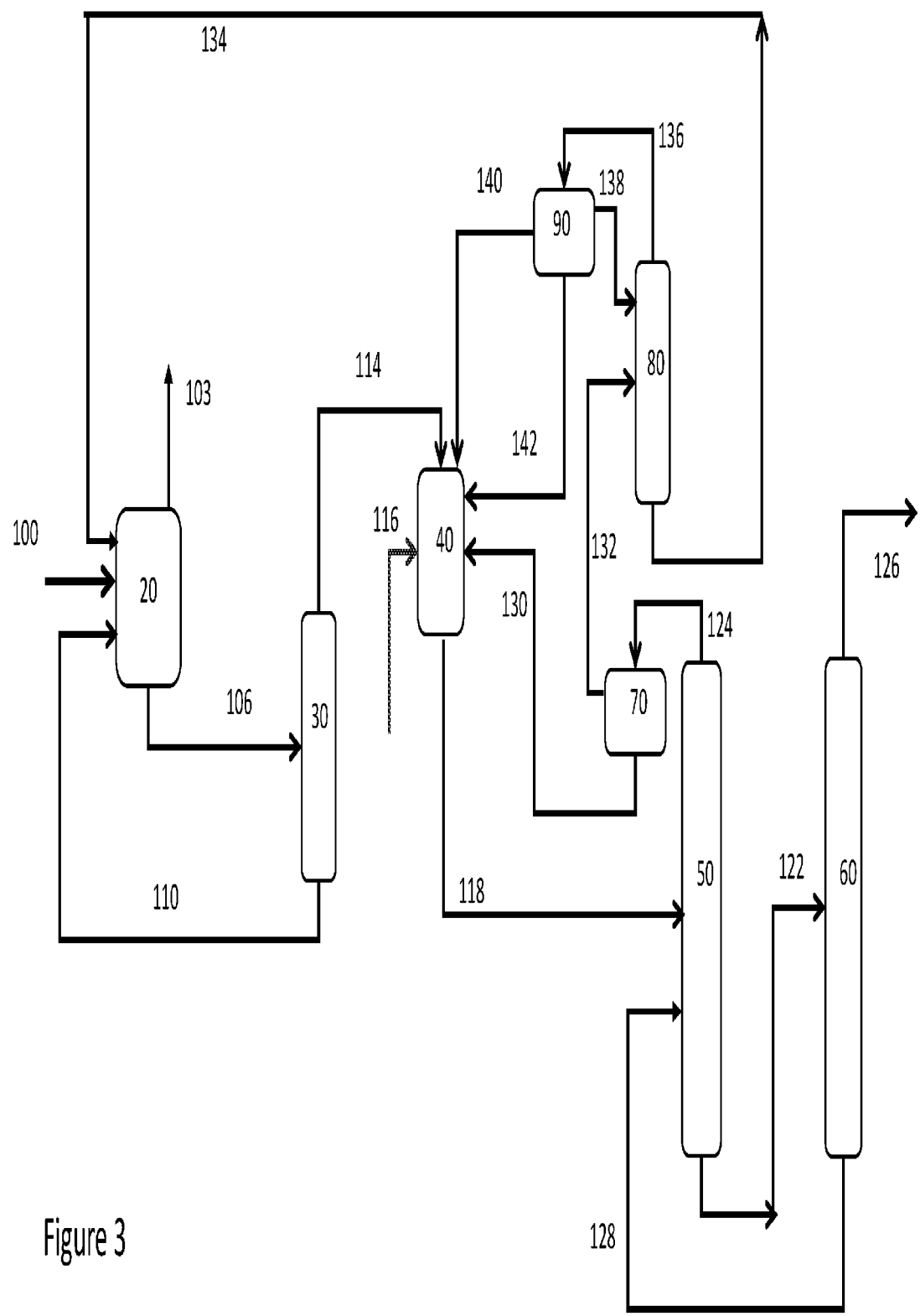
FIG. 3 illustrates a non-limiting process flow diagram of the production of formic acid via dehydrogenative coupling of methanol and 2-butanol.

FIG. 3 illustrates a non-limiting process flow diagram of the production of formic acid via dehydrogenative coupling of methanol and 2-butanol. Methanol 100 is fed to dehydrogenative coupling (DHC) zone 20 along with catalyst recycle 110 and dry 2-butanol recycle 134. Make-up 2-butanol feed is not shown. Hydrogen 103 and DHC effluent 106, comprising 2-butanol, 2-butyl formate, and catalyst, exits DHC reactor 20 and feeds catalyst separation zone 30. Catalyst recycle 110 comprises the homogeneous catalyst and is recycled back to DHC reactor 20. Catalyst purge 112 is not shown.

Formate ester mixture 114 from catalyst separation zone 30 comprises 2-butyl formate. Formate ester mixture 114 and water 116 are fed to hydrolysis reactor 40. Hydrolysis effluent 118 comprises formic acid, 2-butyl formate, 2-butanol, and water and is fed to first distillation column 50. First distillation column 50 may be operated at an operating pressure of around 4 bara with a corresponding bottoms temperature around 155° C. and a first bottoms 122 composition close to the formic acid/water azeotrope (about 80 wt. % formic acid/20 wt. % water). First bottoms 122 is fed to second distillation column 60. Second distillation column 60 may be operated at an operating pressure of around 0.1 bara with a corresponding bottoms temperature around 50° C. and a second bottoms 128 composition close to the corresponding formic acid/water azeotrope (about 70 wt. % formic acid/30 wt. % water). Second bottoms 128 is recycled to first distillation column 50. Second distillate 126 comprises formic acid. Typically, second distillate 126 comprises at least 75 wt. % formic acid and can comprise greater than 99 wt. % formic acid.

First vapor 124 is condensed and fed to decanter 70 wherein two phases form. Recycle 130, comprising water, is recycled to hydrolysis reactor 40. Organic stream 132, comprising 2-butyl formate and 2-butanol, is fed to third distillation column 80. Third bottoms 134, comprising dry 2-butanol, is recycled to DHC reactor 20. Third vapor 136, comprising 2-butyl formate, 2-butanol, and water is condensed and fed to decanter 90 wherein two phases form. Recycle 142, comprising water, is recycled to hydrolysis reactor 40. Recycle 140, comprising 2-butyl formate and 2-butanol, is also recycled to hydrolysis reactor 40. Reflux 138, comprising 2-butyl formate and 2-butanol is fed to the top of third distillation column 80.

The invention can be further illustrated by the following examples of preferred embodiments thereof, although it will be understood that these examples are included merely for purposes of illustration and are not intended to limit the scope of the invention.

EXAMPLES 95 wt. % and 98 wt. % Formic acid, methyl formate (MF), and alcohols were purchased and used without further processing.

Analytical Method

Process samples were analyzed using a Shimadzu gas chromatograph (GC) Model 2010 (or equivalent) equipped with a heated split injector (250° C.) and a flame ionization detector (250° C.). A capillary GC column coated with 100% dimethylpolysiloxane (such as DB-1 or equivalent) with dimension of 60-meter×0.32-mm ID×1.0-micron film thickness was employed. Helium was used as the carrier gas with an initial column head pressure of 11.5 psi and an initial column flow of 1.30 mL/minute while the carrier gas linear velocity of 20 cm/second was maintained constant. The GC oven temperature program was as follows: the initial oven temperature was set at 50° C. and was held for 10 minutes, the oven was ramped up to 250° C. at 4° C./minute and was held at 250° C. for 15 minute (the total run time was 45 mins). 1.0-uL of the prepared sample solution was injected with a split ratio of 40:1. EZ-Chrom Elite chromatography data system software was used for data acquisition and data processing. The sample preparation was done by weighing 0.03 g (accurate to 0.1 mg) of sample in a GC vial and adding 200.0-uL of ISTD solution (1% by volume of nonane in pyridine) and 1000-uL of BSTFA (N, O-bis(trimethylsilyl) trifluoroacetamide) with 1% TMCS (trimethylchlorosilane) to the GC vial. The content was heated at 80° C. for 30 minutes to ensure complete derivatization.

In order to calibrate the GC area counts to actual compositions, a response factor was determined independently for each component of interest. Samples of the components of interest with known concentrations were prepared and analyzed. The known concentrations were plotted against the GC area counts: the slope of this graph is the response factor. At least in part, because of the independent calibration of each component, the sum of GC wt. %'s does not always add to unity, due to errors in calibration.

The percentage of free formic acid is calculated as the moles of equilibrium formic acid divided by the sum of the moles of initial formic acid and alcohol formate ester, multiplied by 100. The equilibrium constant, $K_x$, is calculated as $K_x=(x_{FA}*x_{OH})/(x_{FE}*x_{H2O})$. $x_{FA}$ is the mole fraction of formic acid, $x_{OH}$ is the mole fraction of the alcohol, $x_{FE}$ is the mole fraction of the formate ester of the alcohol and $x_{H2O}$ is the mole fraction of water. All mole fractions are based upon measurement at equilibrium.

Initial Screening Experiments

In order to approximate which formate esters would have more favorable hydrolysis equilibrium characteristics and higher conversion of the formate ester to formic acid, as series of screening experiments were conducted. Because the alcohols are more readily available than the corresponding formate ester, potential alcohols and formic acid were mixed at elevated temperature and allowed to come to equilibrium. Those with more favorable equilibrium characteristics than that of methyl formate hydrolyzed to formic acid and methanol were considered for further experimentation.

Example 1—Equilibration of Methanol with Formic Acid 5 grams of methanol was initially mixed with an equimolar amount of 95 wt. % formic acid (molar ratio of methanol to formic acid was 1/1 initially) and added to a sealed thick-walled vial. The vial was heated to 80° C. and held with mixing for 24 hours at the autogenous pressure to ensure equilibrium conversion. The resulting reaction products were sampled and analyzed by gas chromatography to determine composition. The percentage of the free formic acid present at equilibrium and the molar equilibrium ratio, $K_x$, were calculated from the analytical data and are presented in Table 1.

Examples 2-14—Equilibration of Primary, Secondary and Tertiary Alkanols with Formic Acid Example 1 was repeated with the alcohols listed in Table 1. The percentage of the free formic acid present at equilibrium and the molar equilibrium ratio, $K_x$, were calculated from the analytical data and are presented in Table 1. The molar hydrolysis equilibrium ratio and resulting percentage of free formic acid is much higher for secondary alcohols ($K_x$ from 0.71 to 149 and percentage of free formic acid from 46% to 54%) and tertiary alcohols ($K_x$ from 13.6 to 14 and percentage of free formic acid of 79%) as compared to methanol ($K_x$ of 0.18 and percentage of free formic acid of 30%).

TABLE 1

Equilibration results for Examples 1-14

| Example | Alcohol (ROH) | ROH Type | Kx | % free formic acid at equilibrium |
|---|---|---|---|---|
| 1 | Methanol | primary | 0.18 | 30% |
| 2 | Isopropanol | secondary | 0.71 | 46% |
| 3 | n-butanol | primary | 0.29 | 35% |
| 4 | Isobutanol | primary | 0.32 | 36% |
| 5 | 2-butanol | secondary | 0.70 | 46% |
| 6 | Tert-butanol | tertiary | 14.0 | 79% |
| 7 | 1-methylcyclohexanol | tertiary | 13.6 | 79% |
| 8 | 2,4-dimethyl-3-pentanol | secondary | 1.05 | 51% |
| 9 | 1-ethoxy-2-propanol | secondary | 1.37 | 54% |
| 10 | 1-methoxy-2-propanol | secondary | 1.35 | 54% |
| 11 | 1-propoxy-2-propanol | secondary | 1.20 | 52% |
| 12 | 1-phenoxy-2-propanol | Secondary | 1.07 | 51% |
| 13 | DEG monomethyl ether | Primary | 0.80 | 47% |
| 14 | Phenol | Secondary | 149 | 92% |

Synthesis of Formate Esters

Various formate esters used in the hydrolysis examples were produced by carbonylating the corresponding alcohols or by esterifying the corresponding alcohol with formic acid. The method for producing the formate ester was strictly chosen based upon ease of making each particular formate ester.

Example P1. Preparation of Isopropyl Formate Via Carbonylation of Isopropanol Isopropyl formate was synthesized via base-catalyzed carbonylation of isopropanol with carbon monoxide. The following procedure is representative of the synthesis procedure used herein. 18,927 grams of a solution of 2.8 wt. % potassium isopropoxide in isopropanol was prepared from potassium methoxide/methanol solution and isopropanol by distillation in a 50-liter glass flask fitted with a glass vacuum-jacketed packed column (2.5 cm ID×60 cc length, Pro-Pak® Hastelloy packing) reflux head, heating mantle, nitrogen purge, and cooling water condenser. 1893 grams of a 20 wt. % solution of potassium methoxide in methanol and 18,800 grams of dry isopropanol were added to the distillation flask. The mixture was brought to the boiling point, the reflux head was set to 2/1 reflux and methanol removed as distillate. The distillation was continued until methanol content of the base material was less than 0.1 wt. % by GC analysis. The isopropoxide solution described above was transferred to a 38-liter Hastelloy C276 autoclave, fitted with a heating mantle, magnetic drive agitator, CO and $CO_2$ gas supply lines. The autoclave was purged with dry nitrogen, then CO, and then pressurized to 10.44 MPa (absolute) with CO. The reactor was heated to 30° C. and stirred at 1000 rpm for 24 hours. The reactor was cooled to room temperature, CO vented, and then the vessel was pressurized with $CO_2$ to 1.04 MPa to neutralize the potassium isopropoxide catalyst and form insoluble potassium carbonate. The reactor contents were filtered to remove potassium carbonate. The product isopropyl formate mixture, 26,800 grams, was found by GC analysis to be 95 wt. % isopropyl formate, 5 wt. % isopropanol, with traces of formic acid and water.

Example P2. Preparation of 2-Butyl Formate Ester Via Esterification of 2-Butanol with Formic Acid 2-Butyl formate was synthesized via formic acid-catalyzed esterification of 2-butanol with formic acid. The following procedure is representative of the synthesis procedure used herein. 19,321 grams of 2-butanol and 13,604 grams of formic acid were charged to a 50-liter glass flask fitted with a glass vacuum-jacketed packed column (2.5 cm ID×60 cc length, Pro-Pak® Hastelloy packing) Dean-Stark trap, heating mantle, nitrogen purge, 5-liter distillate receiver, and cooling water condenser. N-Hexane was added to the reaction flask (480 grams) and to the Dean-Stark trap. The mixture was brought to the boiling point, esterification commenced, and the water of reaction was removed as the n-hexane-water azeotrope. This azeotrope separated into two layers in the Dean-Stark trap, with the hexane layer returned to the column, and water removed periodically from the trap. The distillation was continued until water removal was complete (about 4700 grams of water). The pot temperature was increased and the hexane removed from the pot, with a small amount of 2-butyl-formate ester removed last to ensure a hexane-free base material. A total of 22,800 grams of 2-butyl formate was produced, with a composition of 94.5 wt. % 2-butyl formate, 0.8 wt. % 2-butanol, 0.2 wt. % water, 4.5 wt. % formic acid, and less than 0.1 wt. % n-hexane by GC analysis.

Hydrolysis of Formate Esters

Hydrolysis of isopropyl formate and 2-butyl formate were carried out to determine conversion at various conditions. All experiments in this section were done in a 100-ml hastelloy autoclave fitted with a band heater, magnetic drive impeller with pitched blades, cooling water coil, N2 purge, and sampling port. The desired charge of formate ester, alcohol, formic acid, and water were added to the autoclave, purged with N2 and pressurized to 30 to 40 bara with N2. The reactor contents were brought to the desired temperature and maintained at said temperature for 2-4 hours. The autoclave was cooled rapidly to stop re-equilibration upon cooling by removing the band heater and opening water flow to the cooling coil. Once at room temperature, the autoclave was opened, contents transferred to a glass jar, and sampled for GC analysis to determine composition.

Example 15—Hydrolysis of Isopropyl Formate

Isopropyl formate (95 wt. % isopropyl formate, 5 wt. % isopropanol, prepared as in Example P1), isopropanol, water, and a small amount of formic acid were added to a 100-ml hastelloy autoclave in the proportions given in Table 2. The autoclave was heated to 120° C., pressurized to 30 bara, and held with mixing for 4 hours. The reactor was cooled, and the resulting reaction product was sampled and analyzed by gas chromatography to determine composition. Conversion to free formic acid and the molar equilibrium ratio, Kx, were calculated as given above.

Examples 16-18—Hydrolysis of Isopropyl Formate and Methyl Formate

Example 15 was repeated with the amounts the formates and amounts of water and alcohol as given in Table 2. Under the same conditions (i.e., molar ratio of ester to water, molar ratio of ester to formic acid, molar ratio of ester to alcohol, temperature, and pressure) the conversion of methyl formate to free formic acid was 32% and 28%, respectively at 1.82/1 and 1.42/1 molar ratios of water/methyl formate whereas the conversion of iso-propyl formate to free formic acid was 56% and 54%, respectively at 1.82/1 and 1.42/1 molar ratios of water/iso-propyl formate.

TABLE 2

Hydrolysis of formate esters of Examples 16-18

| | Ex 15 | Ex 16 | Ex 17 | Ex 18 |
|---|---|---|---|---|
| Formate Input, grams | P1 | P1 | MF | MF |
| 98 wt. % formic acid | 0.092 | 0.097 | 0.092 | 0.097 |
| Water | 3.44 | 2.83 | 3.44 | 2.83 |
| Formate | 9.24 | 9.74 | 6.30 | 6.64 |
| Isopropanol | 2.31 | 2.44 | | |
| Methanol | 0 | 0 | 1.23 | 1.31 |
| water/Ester molar ratio | 1.82/1 | 1.42/1 | 1.82/1 | 1.42/1 |
| Alcohol/ester molar ratio | 0.37/1 | 0.37/1 | 0.37/1 | 0.37/1 |
| Results | | | | |
| Conversion to free formic | 56% | 54% | 32% | 28% |

TABLE 2-continued

Hydrolysis of formate esters of Examples 16-18

|  | Ex 15 | Ex 16 | Ex 17 | Ex 18 |
|---|---|---|---|---|
| acid |  |  |  |  |
| Molar ratio at equilibrium, $K_x$ | 0.54 | 0.57 | 0.21 | 0.19 |

Example 19—Hydrolysis of 2-Butyl Formate

A mixture comprising 2-Butyl formate (94.47 wt. % 2-butyl formate, 0.83 wt. % 2-butanol, 0.18 wt. % water, 4.52 wt. % formic acid, prepared as in Example P2), water, and 2-butanol were added to a 100-ml hastelloy autoclave in the proportions given in Table 3. The autoclave was heated to 130° C., pressurized to 40 bara, and held with mixing for 4 hours. The reactor was cooled, and the resulting reaction product was sampled and analyzed by gas chromatography to determine composition. Conversion to free formic acid and the molar equilibrium ratio, Kx, were calculated as given above and are presented in Table 3.

Examples 20-23—Hydrolysis of 2-Butyl Formate

Example 19 was repeated adding the amount of 2-butyl formate, 2-butanol, and water as given in Table 3. Conversion to free formic acid and the molar equilibrium ratio, Kx, were calculated as given above and are presented in Table 3. The conversion to free formic acid increased from 42.1% to 59.7% as the water to 2-butyl formate molar ratio increased from 1.46/1 to 3/1.

TABLE 3

Hydrolysis of 2-Butyl Formate of Examples 19-23

|  | Ex 19 | Ex 20 | Ex 22 | Ex 22 | Ex 23 |
|---|---|---|---|---|---|
| Input, grams |  |  |  |  |  |
| 2-Butyl formate | 22.60 | 23.56 | 21.75 | 19.88 | 22.56 |
| Water | 5.51 | 5.71 | 7.95 | 7.26 | 11.27 |
| 2-butanol | 6.90 | 5.74 | 5.30 | 7.85 | 5.51 |
| water/Ester molar ratio | 1.84/1 | 1.46/1 | 2.2/1 | 2.2/1 | 3/1 |
| Alcohol/ester molar ratio | 0.37/1 | 0.37/1 | 0.37/1 | 0.59/1 | 0.39/1 |
| Results |  |  |  |  |  |
| Conversion to free formic acid | 49.1% | 42.1% | 49.0% | 46.2% | 59.7% |
| Molar ratio at equilibrium, $K_x$ | 0.55 | 0.52 | 0.516 | 0.51 | 0.56 |

Examples 24-27—Hydrolysis of 2-Butyl Formate

Example 19 was repeated using a mixture comprising 2-Butyl formate of the composition, 93.69 wt. % 2-butyl formate, 0.26 wt. % 2-butanol, 0.06 wt. % water, 4.76 wt. % formic acid, prepared as in Example P2 and adding the amount of 2-butyl formate, 2-butanol, and water as given in Table 4. Conversion to free formic acid and the molar equilibrium ratio, Kx, were calculated as given above and are presented in Table 4.

TABLE 4

Hydrolysis of 2-Butyl Formate of Examples 24-27

|  | EX 24 | Ex 25 | EX 26 | Ex 27 |
|---|---|---|---|---|
| Temperature, ° C. | 130 | 130 | 90 | 90 |
| Input, grams |  |  |  |  |
| 2-Butyl formate | 27.10 | 28.478 | 27.10 | 28.478 |
| Water | 8.26 | 6.87 | 8.24 | 6.87 |
| 2-butanol | 0.0 | 0.0 | 0.0 | 0.0 |
| Water:Ester molar ratio | 1.84:1 | 1.46:1 | 1.84:1 | 1.46:1 |
| Alcohol:ester molar ratio | 0.0038:1 | 0.0038:1 | 0.0038:1 | 0.0038:1 |
| Results |  |  |  |  |
| Conversion to free formic acid | 54.6% | 43.8% | 48.9% | 44.0% |
| Molar ratio at equilibrium, $K_x$ | 0.47 | 0.44 | 0.44 | 0.44 |

Metal Distillation Column and General Example Description

For Examples 28 through 35 and 39 through 46, experiments were carried out in a laboratory metal distillation column comprising three flanged column sections (lower two sections, Zr702 pipe—3.37 cm OD, 2.82 cm ID, 122 cm length each; upper section, Hastelloy C276 pipe—2.54 cm OD, 2.36 cm ID, 122 cm length), a reboiler (flanged Zr702 pipe—3.37 cm OD, 2.82 cm ID, 7.5 cm length, expanded to 4.83 cm OD, 4.28 cm ID, 44.5 cm length, approximately 425 ml at 100% fill for calibration of level controller), vapor take off line (flanged Zr702 pipe—3.37 cm OD, 2.82 cm ID, 15 cm length, reduced to 2.69 cm OD, 2.25 cm ID, ~40 cm length), cooling water condenser (jacketed flanged Zr702 pipe—2.69 cm OD, 2.25 cm ID, 40 cm length), and reflux vessel (Hastelloy C276 tubing, 4.83 cm OD, 4.28 cm ID, 44.5 cm length, approximately 100 ml volume). Heat was supplied to the reboiler by two 500-watt band heaters. Column pressure was set by a Badger Research control valve and Rosemount pressure transmitter.

The column was packed with Aldrich® glass helices, coil ID of ~6 mm, to give a packed section of 365 cm in length. Feed ports, consisting of Swagelok® fittings and tubing, were welded to the three packed sections of the column, at 11.4, 57.2, 102.9, 133.4, 181.6, 229.9, 265.4, 290.8, 316.2, and 341.6 cm as measured from the top of the reboiler. All Swagelok fittings on the zirconium parts of the column were Tantaline treated 316 SS, and Hastelloy C276 otherwise. Thermowells (welded, closed end tubing, Zr702 or Hastelloy C276, depending on section material) were provided in the packed column sections at 20.3, 43.2, 66.0, 88.9, 128.3, 151.1, 174.0, 196.9, 219.7, 260.4, 285.8 311.2, 336.6, and 362.0 cm as measured from the top of the reboiler. Two additional thermocouples were provided in the reboiler and vapor line (at 387.4 cm from the reboiler).

The entire column was wrapped in fiberglass tape, electrically driven heat tapes, another layer of fiberglass tape, and a layer of fiberglass wool (3 cm thick) to prevent heat loss and ensure essentially adiabatic operation.

Experiments were conducted in the following manner. The formate ester hydrolysis mixture was metered into the column at the desired rate, along with other desired feeds. The reflux pump was set to the desired rate, and the reboiler energy input adjusted to provide sufficient boilup to reach the target underflow temperature. The underflow take-off rate was adjusted by automatic control of reboiler level. The column was allowed to come to steady state operation (usually 10-24 hours). Cumulative distillate and bottoms samples were collected roughly every 24 hours, weighed, and sampled for GC analysis to determine overall mass and component material balances, conversions, top and bottom compositions, and reflux ratio.

Distillation of Isopropyl Formate Hydrolysis Mixtures

Example 28—Distillation at 6.18 Bara

Isopropyl formate, as prepared in Example P1, was mixed with 1.9 equivalents of water and equilibrated at 90° C. overnight, to give a composition of 23.3 wt. % formic acid, 30.3 wt. % isopropyl formate, 26.7 wt. % isopropanol, and 19.7 wt. % water. The percent of free formic acid in the hydrolysis effluent was calculated as 59.5%. The isopropyl formate hydrolysis effluent was fed to the column via the feed port located at 102.9 cm from the reboiler at 1.0 ml/min. An additional 0.6 equivalents of water was fed to the column via the feed port located at 316.2 cm from the reboiler at 0.083 ml/min. Column pressure was maintained at 6.18 bara at the vapor take-off line. Over the course of the four-day operation, the thermocouple in the reboiler averaged about 167° C., with a reboiler residence time of about 13 hours. Distillation results are given in Table 5. There was no evidence of diisopropyl ether. The high temperature and residence led to significant thermal decomposition of formic acid (to carbon monoxide and water) with carbon monoxide exiting the top of the distillation column. In spite of the formic acid losses to thermal decomposition, overall conversion to free formic acid increased significantly via passage through the distillation column, from 59% in the hydrolysis effluent to 70% or greater in the recovered formic acid/water bottoms stream. Formic acid concentration in the base was relatively low (farther from azeotrope composition than according to the instant invention) due to formic acid decomposition.

TABLE 5

Isopropyl formate hydrolysis effluent distillation—Example 28

|  | Day 1 | Day 2 | Day 3 | Day 4 |
|---|---|---|---|---|
| Overall mass accountability, % | 95.1% | 101.0% | 98.9% | 99.7% |
| Formate molar accountability, % | 89.5% | 95% | 91.3% | 91.7% |
| Isopropyl molar accountability, % | 100% | 105% | 105% | 107% |
| Net % Free formic acid recovered in bottoms | 73% | 72% | 71% | 70% |
| Reflux ratio | 0.8 | 0.8 | 0.8 | 0.8 |
| Distillate composition, wt. % | | | | |
| Formic acid | 0.021% | 0.019% | 0.019% | 0.019% |
| Isopropyl formate | 29.9% | 31.3% | 31.5% | 32.3% |
| Isopropanol | 58.9% | 57.6% | 57.6% | 56.9% |
| Water | 11.2% | 11.1% | 10.9% | 10.8% |
| Bottoms composition, wt. % | | | | |
| Formic acid | 58.0% | 57.3% | 56.9% | 56.5% |
| Isopropyl formate | 0.0% | 0.0% | 0.0% | 0.0% |
| Isopropanol | 0.0% | 0.0% | 0.0% | 0.0% |
| Water | 42.0% | 42.7% | 43.1% | 43.5% |

Example 29—Distillation at 5.15 Bara, No Water Feed

Isopropyl formate, as prepared in Example P1, was mixed with 1.8 equivalents of water and equilibrated at 90° C. overnight, to give a composition of 22.2 wt. % formic acid, 32.5 wt. % isopropyl formate, 26.7 wt. % isopropanol, and 18.6 wt. % water. The percent of free formic acid in the hydrolysis effluent was calculated as 56.5%. The isopropyl formate hydrolysis effluent was fed to the column via the feed port located at 102.9 cm from the reboiler at 1.0 ml/min. No additional water was fed to the column. Column pressure was maintained at 5.15 bara at the vapor take-off line. Over the course of the first four days of operation, the thermocouple in the reboiler averaged about 159° C., with a reboiler residence time of about 13 hours. On the fifth day, the heat input to the reboiler was increased until, the bottom temperature reached 163.5° C. Distillation results are given in Table 6. The higher temperature in the reboiler was shown to increase thermal decomposition of formic acid as evidenced by the reduced accountability of formic acid compared to Days 1-4. Overall conversion to free formic acid increased significantly via passage through the distillation column, from 56% in the hydrolysis effluent to 60-72% or greater in the recovered formic acid/water bottoms stream.

TABLE 6

Isopropyl formate hydrolysis effluent distillation - Example 29

|  | Day 1 | Day 2 | Day 3 | Day 4 | Day 5 |
|---|---|---|---|---|---|
| Overall mass accountability, % | 103% | 104.0% | 102.0% | 103.0% | 103.0% |
| Formate molar accountability, % | 100% | 101% | 105% | 97.3% | 92.5% |
| Isopropyl molar accountability, % | 104% | 100% | 103% | 104% | 110% |
| Net % Free formic acid recovered in bottoms | 70.4% | 60.6% | 66.1% | 63.4% | 72.1% |
| Reflux ratio | 1.5 | 1.5 | 1.5 | 1.4 | 1.4 |
| Distillate composition, wt. % | | | | | |
| Formic acid | 0.0% | 0.0% | 0.0% | 0.0% | 0.1% |
| Isopropyl formate | 35.3% | 45.4% | 40.6% | 36.7% | 30.5% |
| isopropanol | 54.1% | 45.6% | 49.8% | 53.4% | 55.6% |
| Water | 10.6% | 9.0% | 9.6% | 9.8% | 13.8% |
| Bottoms composition, wt. % | | | | | |
| Formic acid | 67.8% | 62.7% | 69.4% | 68.8% | 74.9% |
| Isopropyl formate | 0.0% | 0.0% | 0.0% | 0.0% | 0.0% |
| isopropanol | 0.0% | 0.0% | 0.0% | 0.0% | 0.0% |
| Water | 32.2% | 37.3% | 30.6% | 31.2% | 25.1% |

Example 30—Distillation at 5.15 Bara, Recycle Formic Acid-Water Azeotrope Feed

Isopropyl formate, as prepared in Example P1, was mixed with 1.75 equivalents of water and equilibrated at 90° C. overnight, to give a composition of 21.9 wt. % formic acid, 34.0 wt. % isopropyl formate, 26.0 wt. % isopropanol, and 18.0 wt. % water. The percent free formic acid in the hydrolysis effluent was calculated as 55.2%. The isopropyl formate hydrolysis effluent was fed to the column via the feed port located at 102.9 cm from the reboiler at 1.0 ml/min. A second feed of 66.5 wt. % formic acid, 33.5% water was metered to the column via the feed port located at 57.2 cm from the reboiler at 0.112 ml/min. This feed simulated recycle underflow formic acid/water maximum boiling azeotrope from a low pressure formic acid-distillate producing column.

Column pressure was maintained at 5.15 bara at the vapor take-off line. Over the course of the four-day operation, the thermocouple in the reboiler averaged about 159° C., with a reboiler residence time of about 10 hours. Distillation results are given in Table 7. There was no evidence of formation of diisopropyl ether. The long residence time in the reboiler led to thermal decomposition of formic acid. Overall conversion to free formic acid increased significantly via passage through the distillation column, from 55% in the hydrolysis effluent to 74% or greater in the recovered formic acid/water bottoms stream.

TABLE 7

Isopropyl formate hydrolysis effluent distillation - Example 30

|  | Day 1 | Day 2 | Day 3 | Day 4 |
|---|---|---|---|---|
| Overall mass accountability, % | 98.6% | 98.9% | 99.7% | 99.0% |
| Formate molar accountability, % | 89.7% | 89.7% | 91.0% | 95.0% |
| Isopropyl molar accountability, % | 102% | 103% | 103% | 96% |
| Net % Free formic acid recovered in bottoms | 72.1% | 72.0% | 71.3% | 73.1% |
| Reflux ratio | 1.4 | 1.4 | 1.5 | 1.4 |
| Distillate composition, wt. % |  |  |  |  |
| Formic acid | 0.2% | 0.2% | 0.1% | 0.1% |
| Isopropyl formate | 27.1% | 27.2% | 28.0% | 27.9% |
| Isopropanol | 55.6% | 55.2% | 54.7% | 54.7% |
| Water | 17.1% | 17.5% | 17.1% | 17.3% |
| Bottoms composition, wt. % |  |  |  |  |
| Formic acid | 77.3% | 77.1% | 77.2% | 77.3% |
| Isopropyl formate | 0.0% | 0.0% | 0.0% | 0.0% |
| Isopropanol | 0.0% | 0.0% | 0.0% | 0.0% |
| Water | 22.7% | 22.9% | 22.8% | 22.7% |

Example 31—Distillation at 5.15 Bara, Recycle Formic Acid-Water Azeotrope Feed

Example 30 was repeated except the reboiler level was controlled to give a reboiler residence time of about 6 hours. Distillation results are given in Table 8. There was no evidence of formation of diisopropyl ether. The shorter residence time in the reboiler reduced the amount of thermal decomposition of formic acid. Overall conversion to free formic acid increased significantly via passage through the distillation column, from 55% in the hydrolysis effluent to greater than 70% in the recovered formic acid/water bottoms stream.

TABLE 8

Isopropyl formate hydrolysis effluent distillation - Example 31

|  | Day 1 | Day 2 | Day 3 | Day 4 | Day 5 |
|---|---|---|---|---|---|
| Overall mass accountability, % | 103% | 99.9% | 99.9% | 98.9% | 100% |
| Formate molar accountability, % | 100.1% | 93.1% | 92.9% | 90.3% | 92.1% |
| Isopropyl molar accountability, % | 101% | 98% | 97.5% | 97% | 98.6% |
| Net % Free formic acid recovered in bottoms | 72.5% | 70.8% | 71.1% | 70.2% | 70.6% |
| Reflux ratio | 1.4 | 1.4 | 1.4 | 1.4 | 1.4 |
| Distillate composition, wt. % |  |  |  |  |  |
| Formic acid | 0.1% | 0.1% | 0.0% | 0.1% | 0.1% |
| Isopropyl formate | 31.0% | 30.9% | 30.9% | 30.3% | 30.1% |
| Isopropanol | 52.3% | 52.3% | 52.9% | 51.9% | 51.9% |
| Water | 16.5% | 16.7% | 16.2% | 17.7% | 17.9% |
| Bottoms composition, wt. % |  |  |  |  |  |
| Formic acid | 74.8% | 72.6% | 71.5% | 71.9% | 73.0% |
| Isopropyl formate | 0.0% | 0.0% | 0.0% | 0.0% | 0.0% |
| Isopropanol | 0.0% | 0.0% | 0.0% | 0.0% | 0.0% |
| Water | 25.2% | 27.4% | 28.5% | 28.1% | 27.0% |

Example 32—Distillation at 4.11 Bara, Recycle Formic Acid-Water Azeotrope Feed

Example 30 was repeated except that column pressure was maintained at 4.11 bara at the vapor take-off line and the reboiler residence time was about 5 hours. Over the course of the six-day operation, the thermocouple in the reboiler averaged about 153° C. Distillation results are given in Table 9. There was no evidence of formation of diisopropyl ether. The shorter residence time and lower temperature in the reboiler essentially eliminated thermal decomposition of formic acid. Overall conversion to free formic acid increased significantly via passage through the distillation column, from 55% in the hydrolysis effluent to greater than 60% in the recovered formic acid/water bottoms stream.

TABLE 9

Isopropyl formate hydrolysis effluent distillation - Example 32

|  | Day 1 | Day 2 | Day 3 | Day 4 | Day 5 | Day 6 |
|---|---|---|---|---|---|---|
| Overall mass acc, % | 103% | 99.8% | 103% | 103% | 104% | 102% |
| Formate molar acc, % | 106% | 97.9% | 103% | 102% | 103% | 99.5% |
| Isopropyl molar acc, % | 92.4% | 102% | 105% | 103% | 103% | 103% |
| Net % Free formic acid recovered in bottoms | 66.5% | 60.4% | 63.3% | 64.8% | 65.5% | 65.8% |
| Reflux ratio | 1.6 | 1.4 | 1.4 | 1.5 | 1.5 | 1.4 |
| Distillate comp, wt. % |  |  |  |  |  |  |
| Formic acid | 0.0% | 0.0% | 0.0% | 0.0% | 0.0% | 0.0% |
| Isopropyl formate | 45.9% | 44.7% | 43.1% | 41.7% | 41.8% | 39.2% |
| Isopropanol | 44.7% | 46.3% | 48.0% | 49.1% | 49.0% | 50.5% |
| Water | 9.3% | 8.9% | 8.9% | 9.1% | 9.2% | 10.2% |
| Bottoms comp, wt. % |  |  |  |  |  |  |
| Formic acid | 64.9% | 67.8% | 68.7% | 68.4% | 68.4% | 69.6% |
| Isopropyl formate | 0.0% | 0.0% | 0.0% | 0.0% | 0.0% | 0.0% |
| Isopropanol | 0.0% | 0.0% | 0.0% | 0.0% | 0.0% | 0.0% |
| Water | 35.1% | 32.2% | 31.3% | 31.6% | 31.6% | 30.4% |

Example 33—Distillation at 5.15 Bara, Recycle Formic Acid-Water Azeotrope Feed Example 30 was repeated except that the second feed rate was 0.224 ml/min and the reboiler residence time was maintained at about 2.4 hours. Over the course of the six-day operation, the thermocouple in the reboiler averaged about 158° C. Distillation results are given in Table 10. There was no evidence of formation of diisopropyl ether. The shorter residence time in the reboiler nearly eliminated thermal decomposition of formic acid. Overall conversion to free formic acid increased significantly via passage through the distillation column, from 55% in the hydrolysis effluent to greater than 68% in the recovered formic acid/water bottoms stream.

TABLE 10

Isopropyl formate hydrolysis effluent distillation - Example 31

|  | Day 1 | Day 2 | Day 3 | Day 4 | Day 5 | Day 6 |
|---|---|---|---|---|---|---|
| Overall mass acc, % | 104% | 119% | 98.8% | 101% | 102% | 102% |
| Formate molar acc, % | 100.2% | 129% | 90.4% | 97% | 99.2% | 99.8% |
| Isopropyl molar acc, % | 103% | 97.1% | 105% | 103% | 104% | 104% |
| Net % Free formic acid recovered in bottoms | 70.0% | 79.0% | 63.9% | 68.8% | 69.1% | 68.8% |
| Reflux ratio | 0.7 | 0.7 | 0.7 | 0.7 | 0.7 | 0.7 |
| Distillate comp, wt. % | | | | | | |
| Formic acid | 0.0% | 0.0% | 0.1% | 0.2% | 0.1% | 0.1% |
| Isopropyl formate | 34.6% | 32.5% | 34.5% | 32.6% | 33.8% | 33.2% |
| Isopropanol | 53.4% | 53.4% | 50.9% | 50.3% | 51.4% | 50.7% |
| Water | 12.0% | 14.1% | 14.6% | 16.9% | 14.7% | 16.0% |
| Bottoms comp, wt. % | | | | | | |
| Formic acid | 70.1% | 71.3% | 74.1% | 78.8% | 76.1% | 77.3% |
| Isopropyl formate | 0.0% | 0.0% | 0.1% | 0.0% | 0.0% | 0.0% |
| Isopropanol | 0.0% | 0.0% | 0.0% | 0.0% | 0.0% | 0.0% |
| Water | 29.9% | 28.7% | 25.8% | 21.2% | 23.9% | 22.7% |

Example 34—Amberlyst 15 Resin Mixed with Glass Helices

The upper Hastelloy section of the column as described above was repacked with a combination of 0.6 mm glass helices mixed with Amberlyst®-15 resin in hydrogen form. This resin contains highly acidic sulfonic acid groups on a polystyrene backbone. This section contained a total of 90 grams of resin (washed with water prior to use, but no other treatment). Catalyst deactivation is indicated by sulfur content in the reboiler.

Isopropyl formate, as prepared in Example P1, was mixed with 1.85 equivalents of water and equilibrated at 90° C. overnight, to give a composition of 21.7 wt. % formic acid, 32.4 wt. % isopropyl formate, 26.7 wt. % isopropanol, and 19.0 wt. % water. The percent free formic acid in the hydrolysis effluent was calculated as 56.4%. The isopropyl formate hydrolysis effluent was fed to the column via the feed port located at 102.9 cm from the reboiler at 1.0 ml/min. An additional 0.6 equivalents of water was fed to the column via the feed port located at 265.4 cm from the reboiler at 0.083 ml/min. Column pressure was maintained at 6.18 bara at the vapor take-off line. Over the course of the six-day operation, the thermocouple in the reboiler averaged about 167° C., with a reboiler residence time of about 9 hours. Distillation results are given in Table 11. Overall conversion to free formic acid increased significantly via passage through the distillation column, from 56% in the hydrolysis effluent to 83% or greater in the recovered formic acid/water bottoms stream. However, due to high temperatures in the catalyst-containing section (133-155° C.), decomposition of the Amberlyst-15 resin, as indicated by ppm sulfur detected in the base product, was rapid. Approximately 9% of the sulfonic acid groups were lost over the course of the 6 days of operation. In addition, significant amounts of diisopropyl ether were found in the distillate. About 7 mole % of the isopropyl feed moieties were converted into diisopropyl ether.

TABLE 11

Isopropyl formate hydrolysis effluent distillation - Example 34

|  | Day 1 | Day 2 | Day 3 | Day 4 | Day 5 | Day 6 |
|---|---|---|---|---|---|---|
| Overall mass acc, % | 100.0% | 99.6% | 100.0% | 100.7% | 100.1% | 100.0% |
| Formate molar acc, % | 101.1% | 101.2% | 101.2% | 101.1% | 101.4% | 101.1% |
| Isopropyl molar acc, %* | 88.5% | 88.2% | 88.9% | 88.6% | 88.2% | 88.5% |
| Net % Free formic acid recovered in bottoms | 88.50% | 84.70% | 83.70% | 83% | 82.80% | 82.90% |
| Reflux ratio | 0.8 | 0.8 | 0.8 | 0.8 | 0.9 | 0.9 |
| Distillate comp, wt. % | | | | | | |
| Formic acid | 0.1% | 0.1% | 0.0% | 0.0% | 0.0% | 0.0% |
| Isopropyl formate | 15.0% | 22.0% | 23.7% | 24.6% | 24.7% | 24.9% |
| Isopropanol | 70.6% | 66.9% | 65.4% | 65.1% | 64.2% | 64.4% |
| Water | 14.3% | 11.0% | 10.8% | 10.3% | 11.1% | 10.7% |
| Diisopropyl ether | 1.9% | 4.6% | 5.2% | 5.4% | 5.4% | 5.3% |

TABLE 11-continued

Isopropyl formate hydrolysis effluent distillation - Example 34

|  | Day 1 | Day 2 | Day 3 | Day 4 | Day 5 | Day 6 |
|---|---|---|---|---|---|---|
| Bottoms comp, wt. % | | | | | | |
| Formic acid | 56.9% | 58.3% | 59.1% | 58.3% | 57.8% | 58.1% |
| Isopropyl formate | 0.0% | 0.0% | 0.0% | 0.0% | 0.0% | 0.0% |
| Isopropanol | 0.0% | 0.0% | 0.0% | 0.0% | 0.0% | 0.0% |
| Water | 43.1% | 41.7% | 40.9% | 41.7% | 42.2% | 41.9% |
| Diisopropyl ether | 0.0% | 0.1% | 0.0% | 0.1% | 0.1% | 0.1% |
| ppm S in base | 191 | 70 | 44 | 33 | 32 | 51 |

*Isopropyl moieties from diisopropyl ether not included in isopropyl molar accountability calculation

Example 35—6.18 Bara Operation in Only Two Zr Sections of Column

The column described above Example 28 was modified by removal of the upper Hastelloy section and operated with hydrolyzed isopropyl formate as feed (with isopropyl formate as prepared in Example P2). The pre-hydrolysis was carried out in a batch stirred 10-liter glass vessel as described in Example 15, producing a hydrolysis mixture comprising 33 wt. % isopropyl formate, 22.1 wt. % formic acid, 26 wt. % isopropanol, 19.2 wt. % water—55.5% as free formic acid). The isopropyl formate hydrolysis effluent was fed to the column via the feed port located at 57.2 cm from the reboiler at 1.0 ml/min. An additional 0.6 equivalents of water was fed to the column via the feed port located at 181.6 cm from the reboiler at 0.083 ml/min. Column pressure was maintained at 6.18 bara at the vapor take-off line. Reflux ratio was set at 2.7. The column was operated in this fashion for two days, with an overall material balance of 101%, formate balance of 91% and isopropyl balance of 99.3%, the thermocouple in the reboiler averaged about 158° C., with a reboiler residence time of about 9 hours. The distillate was found to comprise 44.9 wt. % isopropyl formate, 30.2 wt. % isopropanol, 22.7 wt. % water, 2.1 wt. % formic acid, and the bottoms was found to comprise 13.9 wt. % isopropyl formate, 15.0 wt. % isopropanol, 28.5 wt. % water, 42.7 wt. % formic acid Overall conversion to free formic acid was not increased via passage through the distillation column (remained at approximately 55%), formic acid losses resulted from the high reboiler temperature and residence time, and overall separation of ester/alcohol from formic acid was poor.

Example 36—1 Bara Operation in Glass Column with Added Sulfuric Acid Catalyst This experiment was carried out in a laboratory glass distillation column, comprising a silvered vacuum-jacketed 106-tray Oldershaw column (2.54 cm ID), a reboiler (flanged Hastalloy C276 pipe—3.81 cm ID, 46 cm length, approximately 400 ml at 100% fill for calibration of level controller), silvered, vacuum-jacketed vapor take off line, and 50 ml glass reflux vessel. Heat was supplied to the reboiler by two 500-watt band heaters. Thermocouples were provided in the reboiler, vapor line, and every ten trays.

Experiments were conducted in the following manner. A mixture comprising isopropyl formate and isopropanol (90 wt. %/10 wt. %) was fed on the 27$^{th}$ tray from the reboiler and a water-sulfuric acid mixture (95 wt. %/5 wt. %) supplied on the 82$^{nd}$ tray from the reboiler. The reflux pump was set to the desired rate, and the reboiler energy input adjusted to provide sufficient boilup to reach the target underflow temperature. The underflow take-off rate was adjusted by automatic control of reboiler level. The column was allowed to come to steady state operation (usually 10-24 hours). Cumulative distillate and bottoms samples were collected roughly every 24 hours, weighed, and sampled for GC analysis to determine overall mass and component material balances, conversions, top and bottom compositions, and reflux ratio as shown in Table 12. The bottoms temperature averaged of 104° C. on all days of operation, with a column head pressure of about 0.97 bara. This experiment shows that pre-distillation hydrolysis is needed to increase conversion above about 36% at the low temperatures achievable at atmospheric pressure, even with sulfuric acid catalyst added.

TABLE 12

Distillation with no pre-distillation hydrolysis - Example 36

|  | Day 1 | Day 2 | Day 3 | Day 4 | Day 5 |
|---|---|---|---|---|---|
| Isopropyl formate feed, ml/min | 1 | 1 | 0.5 | 0.5 | 0.5 |
| Sulfuric acid feed, ml/min | 0.77 | 0.77 | 0.385 | 0.385 | 0.385 |
| Overall mass acc, % | 99.4% | 102% | 100.2% | 100.8% | 99.8% |
| Formate molar acc, % | 95.8% | 98.0% | 103.2% | 100.1% | 100.9% |
| Isopropyl molar acc, %* | 94.2% | 91.6% | 94.2% | 94.9% | 94.4% |
| Net % Free formic acid recovered in bottoms | 36.2% | 35.7% | 30.0% | 27.9% | 25.3% |
| Reflux ratio | 0.4 | 0.4 | 0.8 | 0.8 | 0.8 |
| Distillate comp, wt. % | | | | | |
| Bottom phase Formic acid | N/D | N/D | 0.05% | 0.06% | 0.05% |
| Isopropyl formate | N/D | N/D | 2.33% | 0.43% | 1.77% |
| Isopropanol | N/D | N/D | 16.78% | 16.50% | 15.61% |
| Water | N/D | N/D | 77.04% | 80.54% | 80.80% |
| Top phase Formic acid | 0.00% | 0.01% | 0.01% | 0.03% | 0.03% |
| Isopropyl formate | 59.74% | 59.53% | 71.56% | 73.23% | 76.11% |
| Isopropanol | 30.09% | 29.69% | 22.09% | 20.80% | 18.58% |
| Water | 11.90% | 12.28% | 7.84% | 7.34% | 6.21% |
| Bottoms comp, wt. % | | | | | |
| Formic acid | 20.43% | 20.28% | 18.55% | 16.27% | 16.04% |
| Isopropyl formate | 0.00% | 0.00% | 0.00% | 0.00% | 0.00% |
| Isopropanol | 0.00% | 0.00% | 0.00% | 0.00% | 0.00% |
| Water | 73.41% | 73.18% | 75.21% | 76.75% | 76.92% |
| Sulfuric acid | 2.02% | 2.36% | 1.96% | 2.00% | 2.43% |

Example 37—Hydrolysis in Glass Column with Added Sulfuric Acid Catalyst

This experiment was carried out in the same laboratory glass distillation column as Example 36. A mixture comprising isopropyl formate/isopropanol/water (95.3 wt. %/4.3 wt. %/0.1 wt. %) was fed on the 27$^{th}$ tray from the reboiler and a water-sulfuric acid mixture (90 wt. %/10 wt. %) supplied on the 82$^{nd}$ tray from the reboiler. The reflux pump was set to the desired rate, and the reboiler energy input adjusted to provide sufficient boilup to reach the target underflow temperature. The underflow take-off rate was adjusted by automatic control of reboiler level. The column was allowed to come to steady state operation (usually 10-24 hours). The bottoms temperature was increased by additional heat input to the reboiler from an average of 104.5° C. on Days 1 and 2 to 107° C. on Days 3 and 4. The column was operated with a head pressure of about 0.97 bara throughout the four-days of operation. Cumulative distillate and bottoms samples were collected roughly every 24 hours, weighed, and sampled for GC analysis to determine overall mass and component material balances, conversions, top and bottom compositions, and reflux ratio as shown in Table 13. The higher sulfuric acid appeared to lead to formic acid decomposition and did not increase overall conversion to free formic acid appreciably.

TABLE 13

Isopropyl formate hydrolysis effluent distillation - Example 37

|  | Day 1 | Day 2 | Day 3 | Day 4 |
|---|---|---|---|---|
| Isopropyl formate feed, ml/min | 0.5 | 0.5 | 0.5 | 0.5 |
| Sulfuric acid feed, ml/min | 0.385 | 0.385 | 0.385 | 0.385 |
| Overall mass acc, % | 102.1% | 102.7% | 98.1% | 98.7% |
| Formate molar acc, % | 93.7% | 72.2% | 72.4% | 72.0% |
| Isopropyl molar acc, %* | 97.2% | 129% | 119% | 131% |
| Net % Free formic acid recovered in bottoms | 32.3% | 42.1% | 29.8% | 35.5% |
| Reflux ratio | 0.8 | 0.9 | 0.8 | 0.8 |
| Distillate comp, wt. % |  |  |  |  |
| Bottom phase Formic acid | 0.11% | 0.00% | 0.04% | 0.04% |
| Isopropyl formate | 2.17% | 56.37% | 67.29% | 68.69% |
| isopropanol | 18.09% | 32.73% | 24.16% | 23.26% |
| water | 77.09% | 10.98% | 8.92% | 8.35% |
| Top phase Formic acid | 0.05% | N/D | 0.06% | 0.08% |
| Isopropyl formate | 66.46% | N/D | 3.30% | 2.93% |
| isopropanol | 24.97% | N/D | 18.12% | 17.56% |
| water | 9.26% | N/D | 76.10% | 75.65% |
| Bottoms comp, wt.% |  |  |  |  |
| Formic acid | 17.54% | 19.65% | 23.41% | 24.49% |
| Isopropyl formate | 0.00% | 0.00% | 0.00% | 0.00% |
| isopropanol | 0.00% | 0.00% | 0.00% | 0.00% |
| water | 73.78% | 69.65% | 63.97% | 61.22% |
| Sulfuric acid | 3.51% | 4.27% | 4.69% | 14.17% |

Example 38—Pre-Hydrolysis and Hydrolysis in Glass Column with Amberlyst 15 Catalyst This experiment was carried out to determine the efficacy of pre-hydrolysis, followed by distillation in an atmospheric distillation column packed with a mixture of acidic resin catalyst and Hastelloy C276 packing. The pre-hydrolysis was carried out in a batch stirred 10-liter glass vessel with electrical heating. The reaction vessel was charged with 2437 grams of 95/5 wt. % isopropyl formate/isopropanol, (as prepared in Example P2), 191 grams 98% formic acid, and 875 grams of water (water/formate ester molar ratio of 1.85), heated to 80° C., and held overnight to allow equilibration. The resulting hydrolysis mixture comprised 34 wt. % isopropyl formate, 22.1 wt. % formic acid, 25.3 wt. % isopropanol, 18.5 wt. % water—55.4% as free formic acid). This hydrolysis procedure was repeated as necessary to supply feed to the distillation column described herein.

Distillation operations were conducted in a column configuration comprising a silvered vacuum-jacketed column of 2.54 cm ID, with a bottom section of 25-Oldershaw trays, and a top section of 272 cm length, packed with a mixture of 0.29 kg Amberlyst®-15 hydrogen form strongly acidic resin and 0.275 kg of Pro-pak® Hastelloy 0.3 cm packing); a reboiler (flanged Hastelloy C276 pipe—3.81 cm ID, 46 cm length, approximately 400 ml at 100% fill for calibration of level controller); a silvered, vacuum-jacketed vapor take off line; and 50 ml glass reflux vessel. Heat was supplied to the reboiler by two 500-watt band heaters. Thermocouples were provided in the reboiler, vapor line, and ten thermocouples in the column section, roughly evenly spaced.

During distillation operation, the hydrolysis feed mixture was fed 60 cm above the 25-tray Oldershaw section into the packed section at a rate of 1 ml/min. An additional water feed of 0.082 ml/min water fed 210 cm above the Oldershaw section. The reflux pump was set to the desired rate, and the reboiler energy input adjusted to provide sufficient boilup to reach the target underflow temperature. The underflow take-off rate was adjusted by automatic control of reboiler level. The column was allowed to come to steady state operation (usually 10-24 hours). Cumulative distillate and bottoms samples were collected roughly every 24 hours, weighed, and sampled for GC analysis to determine overall mass and component material balances, conversions, top and bottom compositions, and reflux ratio as shown in Table 14. On all days of operation, the column head pressure was about 0.95-0.97 bara. At end of the 5-day experiment, the combined underflow was tested for sulfur content to determine if the resin was losing sulfonic acid groups. The underflow was found to contain 45 ppm of sulfur, or about 18% of the sulfur contained in the resin catalyst originally.

This experiment shows that overall conversion was significantly increased by reaction in the distillation column, with free formic acid recovered in the bottoms stream above 76 to 86% (increase of about 21 to 31 percentage points above the hydrolysis feed). However, the Amberlyst®-15 resin was found to have lost sulfonic acid groups at a rate of about 3.5% per day of operation.

TABLE 14

Isopropyl formate hydrolysis effluent distillation - Example 38

|  | Day 1 | Day 2 | Day 3 | Day 4 | Day 5 |
|---|---|---|---|---|---|
| Overall mass acc, % | 90% | 88% | 89% | 96% | 93% |
| Formate molar acc, % | 100.7% | 97.4% | 88.9% | 99.2% | 95.1% |
| Isopropyl molar acc, %* | 90.5% | 104.4% | 97.6% | 99.0% | 88.4% |
| Net % Free formic acid recovered in bottoms | 77.6% | 86.2% | 81.7% | 81.0% | 76.8% |
| Reflux ratio | 1.1 | 2.2 | 2.7 | 2.6 | 2.5 |
| Bottoms Temp, Celsius | 103 | 105 | 104.5 | 104.2 | 104.0 |
| Distillate comp, wt. % |  |  |  |  |  |
| Formic acid | 0.06% | 0.08% | 0.05% | 0.04% | 0.04% |
| Isopropyl formate | 34.5% | 28.8% | 20.7% | 23.8% | 27.4% |
| Isopropanol | 55.7% | 60.0% | 69.2% | 68.3% | 63.9% |
| Water | 10.7% | 13.0% | 35.2% | 10.4% | 9.7% |
| Unknowns | N/D | N/D | N/D | N/D | N/D |
| Bottoms comp, wt. % |  |  |  |  |  |
| Formic acid | 60.0% | 73.4% | 66.5% | 59.8% | 57.3% |
| Isopropyl formate | 0.10% | N/D | N/D | N/D | N/D |
| Isopropanol | 0.02% | N/D | N/D | N/D | N/D |
| Water | 38.4% | 26.5% | 35.2% | 42.2% | 43.1% |
| Unknowns | 1.0% | N/D | N/D | N/D | N/D |

Distillation of 2-Butyl Formate Hydrolysis Mixtures

Example 39—Distillation at 4.14 Bara

2-Butyl formate, as prepared in Example P2, was mixed with 1.46 equivalents of water and equilibrated at 130° C. for 4 hours, to give a composition comprising 13.40 wt. % formic acid, 40.47 wt. % 2-butyl formate, 35.23 wt. % 2-butanol, and 11.83 wt. % water. The % free formic acid in the hydrolysis effluent was calculated as 42.4%. The hydrolysis effluent was fed to the column (described above Example 26) via the feed port located at 102.9 cm from the reboiler at 1.064 ml/min. A second feed of water was metered to the column via the feed port located at 316.2 cm from the reboiler at 0.1 ml/min (0.86 moles of water per mole of ester in the unhydrolyzed feed). A third feed of 70 wt. % formic acid, 30 wt. % water was metered to the column via the feed port located at 57.2 cm from the reboiler at 0.155 ml/min. The third feed simulated recycled formic acid/water maximum boiling azeotrope from a low pressure formic acid-distillate producing column (e.g., bottoms 218 of column 60 in FIG. 2). Column pressure was maintained at 4.14 bara at the vapor take-off line. Over the course of the four-day operation, the thermocouple in the reboiler averaged about 152.3-154.3° C., with a reboiler residence time of about 10 hours. Distillation results are given in Table 15. There was no evidence of formation of di-2-butyl ether. On all days, at a reflux ratio of about 0.92-0.98, overall conversion to free formic acid increased via passage through the distillation column from 42.4% in the hydrolysis effluent to about 47-52% in the recovered formic acid/water bottoms stream.

TABLE 15

2-Butyl formate hydrolysis effluent distillation - Example 39

|  | Day 1 | Day 2 | Day 3 | Day 4 |
| --- | --- | --- | --- | --- |
| Overall mass acc, % | 95.7% | 98.0% | 97.4% | 97.2% |
| Formate molar acc, % | 103.98% | 103.55% | 100.52% | 99.24% |
| 2-Butyl molar acc, % | 102.58% | 97.60% | 100.35% | 101.37% |
| Net % Free formic acid recovered in bottoms | 49.8% | 52.0% | 48.5% | 47.5% |
| Reflux ratio | 0.92 | 0.98 | 0.96 | 0.95 |
| Distillate bottom/top phase mass ratio | 0.0000 | 0.0000 | 0.0000 | 0.0000 |
| Reboiler temperature, Celsius | 154.3 | 152.4 | 152.3 | 152.3 |
| Distillate comp, wt. % |  |  |  |  |
| Bottom phase |  |  |  |  |
| Formic acid | No phase | No phase | No phase | No phase |
| 2-Butyl formate | No phase | No phase | No phase | No phase |
| 2-Butanol | No phase | No phase | No phase | No phase |
| Water | No phase | No phase | No phase | No phase |
| Top phase Formic acid | 0.03% | 0.04% | 0.04% | 0.04% |
| 2-Butyl formate | 43.96% | 44.36% | 44.97% | 44.55% |
| 2-Butanol | 46.38% | 46.82% | 47.34% | 47.63% |
| Water | 10.22% | 10.38% | 10.50% | 10.52% |
| Bottoms comp, wt. % |  |  |  |  |
| Formic acid | 76.28% | 64.73% | 63.48% | 63.78% |
| 2-Butyl formate | N/D | N/D | N/D | N/D |
| 2-Butanol | N/D | N/D | N/D | N/D |
| Water | 24.00% | 36.06% | 38.13% | 38.41% |

Example 40—Distillation at 4.14 Bara

Example 39 was repeated, except that the second feed of water was increased to 0.2 ml/min (1.72 moles of water per mole of ester in the unhydrolyzed feed). Over the course of the four-day operation, the bottoms temperature increased from about 153 to 154° C., with a reboiler residence time of about 10 hours. Distillation results are given in Table 16. There was no evidence of formation of di-2-butyl ether. At a reflux ratio of about 0.78-0.83, overall conversion to free formic acid increased via passage through the distillation column from 42.4% in the hydrolysis effluent to about 45-48% in the recovered formic acid/water bottoms stream.

TABLE 16

2-Butyl formate hydrolysis effluent distillation - Example 40

|  | Day 1 | Day 2 | Day 3 | Day 4 |
| --- | --- | --- | --- | --- |
| Overall mass acc, % | 97.3% | 97.3% | 96.1% | 96.8% |
| Formate molar acc, % | 107.86% | 108.32% | 110.53% | 105.97% |
| 2-Butyl molar acc, % | 99.53% | 98.73% | 99.23% | 98.53% |
| Net % Free formic acid recovered in bottoms | 48.2% | 46.9% | 46.6% | 45.4% |
| Reflux ratio | 0.83 | 0.80 | 0.81 | 0.78 |
| Reboiler temperature, Celsius | 153.1 | 153.7 | 153.9 | 154.1 |
| Distillate bottom/top phase mass ratio | 0.1866 | 0.2529 | 0.2533 | 0.2712 |
| Distillate comp, wt. % |  |  |  |  |
| Bottom phase |  |  |  |  |
| Formic acid | 0.05% | 0.06% | 0.06% | 0.05% |
| 2-Butyl formate | 0.54% | 0.65% | 0.64% | 0.63% |
| 2-Butanol | 9.43% | 9.68% | 9.58% | 9.63% |
| Water | 88.82% | 88.36% | 87.86% | 88.35% |
| Top phase Formic acid | 0.05% | 0.05% | 0.04% | 0.04% |
| 2-Butyl formate | 45.10% | 43.85% | 46.36% | 42.86% |
| 2-Butanol | 46.62% | 47.81% | 47.35% | 47.64% |
| Water | 10.35% | 10.74% | 10.56% | 10.52% |
| Bottoms comp, wt. % |  |  |  |  |
| Formic acid | 66.92% | 68.76% | 71.02% | 71.31% |
| 2-Butyl formate | N/D | N/D | N/D | N/D |
| 2-Butanol | N/D | N/D | N/D | N/D |
| Water | 33.63% | 31.99% | 28.72% | 28.15% |

Example 41—Distillation at 4.14 Bara

Example 39 was repeated, except that the second feed of water was increased to 0.2 ml/min (1.72 moles of water per mole of ester in the unhydrolyzed feed) and the reboiler temperature was increased to increase formic acid concentration in the underflow product. Over the course of the four-day operation, the reboiler temperature averaged about 155° C., with a reboiler residence time of about 10 hours. Distillation results are given in Table 17. There was no evidence of formation of di-2-butyl ether. At a reflux ratio of about 0.77, overall conversion to free formic acid increased via passage through the distillation column from 42.4% in the hydrolysis effluent to about 43.5-44.5% in the recovered formic acid/water bottoms stream.

TABLE 17

2-Butyl formate hydrolysis effluent distillation - Example 41

|  | Day 1 | Day 2 | Day 3 | Day 4 |
| --- | --- | --- | --- | --- |
| Overall mass acc, % | 96.0% | 96.0% | 96.0% | 96.0% |
| Formate molar acc, % | 104.07% | 105.08% | 106.39% | 102.94% |
| 2-Butyl molar acc, % | 98.00% | 98.20% | 97.55% | 98.32% |
| Net % Free formic acid recovered in bottoms | 43.6% | 43.5% | 44.5% | 44.4% |
| Reflux ratio | 0.77 | 0.76 | 0.76 | 0.77 |
| Reboiler temperature, Celsius | 155.3 | 155.0 | 155.0 | 154.8 |

TABLE 17-continued

2-Butyl formate hydrolysis effluent distillation - Example 41

|  | Day 1 | Day 2 | Day 3 | Day 4 |
|---|---|---|---|---|
| Distillate bottom/ top phase mass ratio | 0.3021 | 0.3144 | 0.3077 | 0.2862 |
| Distillate comp, wt. % | | | | |
| Bottom phase Formic acid | 0.06% | 0.05% | 0.05% | 0.05% |
| 2-Butyl formate | 0.58% | 0.60% | 0.64% | 0.54% |
| 2-Butanol | 9.65% | 9.68% | 9.60% | 9.50% |
| Water | 89.17% | 88.15% | 87.95% | 87.57% |
| Top phase Formic acid | 0.05% | 0.05% | 0.04% | 0.04% |
| 2-Butyl formate | 42.47% | 42.74% | 42.41% | 42.14% |
| 2-Butanol | 47.26% | 47.27% | 47.06% | 47.44% |
| Water | 10.55% | 9.95% | 10.43% | 10.60% |
| Bottoms comp, wt. % | | | | |
| Formic acid | 75.73% | 77.56% | 77.58% | 75.57% |
| 2-Butyl formate | N/D | N/D | N/D | N/D |
| 2-Butanol | N/D | N/D | N/D | N/D |
| Water | 24.29% | 23.22% | 22.95% | 24.10% |

Example 42—Distillation at 4.14 Bara

Examples 39 was repeated, except that the second feed of water was shut off completely. Over the course of the four-day operation, the thermocouple in the reboiler averaged about 155.1° C., with a reboiler residence time of about 10 hours. Distillation results are given in Table 18. There was no evidence of formation of di-2-butyl ether. At a reflux ratio of about 0.93 to 0.95, overall conversion to free formic acid decreased via passage through the distillation column from 42.4% in the hydrolysis effluent, generally to 40% or less in the recovered formic acid/water bottoms stream. Formic acid accountability was low, presumably due to high reboiler concentrations and residence times.

TABLE 18

2-Butyl formate hydrolysis effluent distillation - Example 42

|  | Day 1 | Day 2 | Day 3 | Day 4 |
|---|---|---|---|---|
| Overall mass acc, % | 95.9% | 94.0% | 93.6% | 93.2% |
| Formate molar acc, % | 84.97% | 83.30% | 83.93% | 81.71% |
| 2-Butyl molar acc, % | 95.13% | 97.09% | 95.43% | 95.35% |
| Net % Free formic acid recovered in bottoms | 40.4% | 40.4% | 42.3% | 38.7% |
| Reflux ratio | 0.93 | 0.95 | 0.96 | 0.95 |
| Reboiler temperature, Celsius | 155.1 | 155.1 | 155.1 | 155.2 |
| Distillate bottom/ top phase mass ratio | 0.0408 | 0.0043 | 0.0000 | 0.0108 |
| Distillate comp, wt. % | | | | |
| Bottom phase Formic acid | 0.05% | 0.31% | N/D | 0.05% |
| 2-Butyl formate | 0.59% | 0.35% | N/D | 0.49% |
| 2-Butanol | 10.25% | 10.48% | N/D | 9.50% |
| Water | 90.95% | 86.93% | N/D | 86.49% |
| Top phase Formic acid | 0.04% | 0.04% | 0.03% | 0.03% |
| 2-Butyl formate | 39.59% | 39.05% | 38.76% | 39.53% |
| 2-Butanol | 47.52% | 48.51% | 48.17% | 47.49% |
| Water | 10.77% | 10.87% | 10.97% | 10.76% |
| Bottoms comp, wt. % | | | | |
| Formic acid | 74.78% | 76.89% | 77.42% | 76.81% |
| 2-Butyl formate | N/D | N/D | N/D | N/D |
| 2-Butanol | N/D | N/D | N/D | N/D |
| Water | 22.61% | 22.07% | 22.31% | 22.02% |

Example 43—Distillation at 4.11 Bara

2-Butyl formate, as prepared in Example P2, was mixed with water, formic acid, and 2-butanol to produce a simulated hydrolysis effluent (closely mimicking an equilibrated hydrolysis mixture produced at 130° C. with 1.46 equivalents of water), to give a composition comprising of 13.47 wt. % formic acid, 35.58 wt. % 2-butyl formate, 36.84 wt. % 2-butanol, and 13.32 wt. % water. The % free formic acid in the simulated hydrolysis effluent was calculated as 43.3%. The simulated 2-butyl formate hydrolysis effluent was fed to the column via the fee port located at 102.9 cm from the reboiler at 1.064 ml/min. A second feed of 70 wt. % formic acid, 30 wt. % water was metered to the column via the fee port located at 57.2 cm from the reboiler at 0.155 ml/min. The second feed simulated recycled formic acid/water maximum boiling azeotrope from a low pressure formic acid-distillate producing column. Column pressure was maintained at 4.14 bara at the vapor take-off line. Over the course of the four-day operation, the reboiler temperature averaged about 155.2-155.4° C., with a reboiler residence time of about 10 hours. Distillation results are given in Table 19. There was no evidence of formation of di-2-butyl ether. On all days, at a reflux ratio of about 0.5, overall conversion to free formic acid changed very little via passage through the distillation column from 45.7% in the hydrolysis effluent to about 44-47% in the recovered formic acid/water bottoms stream.

TABLE 19

2-Butyl formate hydrolysis effluent distillation - Example 43

|  | Day 1 | Day 2 | Day 3 | Day 4 |
|---|---|---|---|---|
| Overall mass acc, % | 94.4% | 94.8% | 95.3% | 93.8% |
| Formate molar acc, % | 88.80% | 91.17% | 92.20% | 87.90% |
| 2-Butyl molar acc, % | 99.22% | 99.51% | 98.93% | 101.74% |
| Net % Free formic acid recovered in bottoms | 43.7% | 45.2% | 47.0% | 46.8% |
| Reflux ratio | 0.48 | 0.48 | 0.48 | 0.47 |
| Reboiler temperature, Celsius | 155.2 | 155.2 | 155.2 | 155.4 |
| Distillate bottom/ top phase mass ratio | 0.0164 | 0.0152 | 0.0031 | 0.0057 |
| Distillate comp, wt. % | | | | |
| Bottom phase Formic acid | 0.07% | 0.17% | 0.11% | 0.19% |
| 2-Butyl formate | 0.62% | 0.31% | 0.62% | 0.07% |
| 2-Butanol | 9.82% | 9.65% | 10.00% | 7.30% |
| Water | 86.54% | 86.52% | 86.32% | 81.95% |
| Top phase Formic acid | 0.06% | 0.07% | 0.06% | 0.06% |
| 2-Butyl formate | 39.15% | 38.63% | 38.30% | 39.54% |
| 2-Butanol | 48.88% | 49.51% | 49.47% | 48.90% |
| Water | 11.09% | 11.25% | 11.40% | 11.21% |
| Bottoms comp, wt. % | | | | |
| Formic acid | 77.84% | 79.06% | 77.44% | 79.17% |
| 2-Butyl formate | N/D | N/D | N/D | N/D |
| 2-Butanol | N/D | N/D | N/D | N/D |
| Water | 20.23% | 20.25% | 20.97% | 20.13% |

Example 44—Distillation at 4.14 Bara

Example 43 was repeated except that the second feed of 70 wt. % formic acid, 30 wt. % water was metered to the column via the feed port located at 57.2 cm from the reboiler at 0.31 ml/min, the reboiler residence time was maintained at about 5 hours, and the reflux ratio was very low, about 0.21 to 0.26. Distillation results are given in Table 20. There was no evidence of formation of di-2-butyl ether. On all days but one, overall conversion to free formic acid decreased via passage through the distillation column from 43.6% in the hydrolysis effluent to less than 40% in the recovered formic acid/water bottoms stream.

TABLE 20

2-Butyl formate hydrolysis effluent distillation - Example 44

|  | Day 1 | Day 2 | Day 3 | Day 4 |
|---|---|---|---|---|
| Overall mass acc, % | 97.2% | 95.0% | 95.8% | 98.1% |
| Formate molar acc, % | 94.4% | 96.3% | 91.3% | 100.4% |
| 2-Butyl molar acc, % | 96.5% | 93.9% | 97.2% | 97.4% |
| Net % Free formic acid recovered in bottoms | 36.4% | 31.7% | 44.7% | 23.1% |
| Reflux ratio | 0.26 | 0.22 | 0.24 | 0.21 |
| Reboiler temperature, Celsius | 155.4 | 155.4 | 155.4 | 155.5 |
| Distillate bottom/ top phase mass ratio | 0.076 | 0.12 | 0.065 | 0.145 |
| Distillate comp, wt. % | | | | |
| Bottom phase Formic acid | 0.15% | 0.20% | 0.29% | 0.21% |
| 2-Butyl formate | 0.51% | 0.57% | 0.31% | 0.63% |
| 2-Butanol | 8.94% | 8.46% | 9.31% | 8.42% |
| Water | 87.27% | 88.31% | 89.21% | 89.44% |
| Top phase Formic acid | 0.13% | 0.19% | 0.13% | 0.18% |
| 2-Butyl formate | 43.98% | 50.45% | 44.15% | 53.74% |
| 2-Butanol | 43.90% | 40.06% | 45.61% | 38.30% |
| Water | 9.34% | 8.42% | 10.12% | 7.84% |
| Bottoms comp. wt. % | | | | |
| Formic acid | 80.69% | 81.68% | 80.85% | 80.50% |
| 2-Butyl formate | N/D | N/D | N/D | N/D |
| 2-Butanol | N/D | N/D | N/D | N/D |
| Water | 17.89% | 17.48% | 18.23% | 17.40% |

Example 45—Distillation at 4.14 Bara

Example 43 was repeated except that the simulated 2-butyl formate hydrolysis effluent was fed to the column at 2.128 ml/min; the second feed was fed at 0.31 ml/min, and the reboiler residence time was about 2.5 hours. Over the course of the four-day operation, the reboiler temperature averaged about 154.5 to 155.1° C. Distillation results are given in Table 21. There was no evidence of formation of di-2-butyl ether. On all days, at a reflux ratio of about 0.5, overall conversion to free formic acid increased via passage through the distillation column from 43.6% in the hydrolysis effluent to about 47-48% in the recovered formic acid/water bottoms stream.

TABLE 21

2-Butyl formate hydrolysis effluent distillation - Example 45

|  | Day 1 | Day 2 | Day 3 | Day 4 |
|---|---|---|---|---|
| Overall mass acc, % | 97.8% | 98.4% | 98.0% | 98.4% |
| Formate molar acc, % | 98.06% | 97.25% | 94.74% | 94.10% |
| 2-Butyl molar acc, % | 98.85% | 97.97% | 93.21% | 96.16% |
| Net % Free formic acid recovered in bottoms | 47.4% | 47.7% | 48.7% | 46.7% |
| Reflux ratio | 0.47 | 0.47 | 0.49 | 0.47 |
| Reboiler Temperature, Celsius | 155.1 | 154.9 | 154.5 | 154.9 |
| Distillate bottom/ top phase mass ratio | 0.0079 | 0.0033 | 0.0005 | 0.0000 |
| Distillate comp. wt. % | | | | |
| Bottom phase Formic acid | 0.07% | 0.06% | 0.19% | No phase |

TABLE 21-continued

2-Butyl formate hydrolysis effluent distillation - Example 45

|  | Day 1 | Day 2 | Day 3 | Day 4 |
|---|---|---|---|---|
| 2-Butyl formate | 0.41% | 0.59% | 1.02% | No phase |
| 2-Butanol | 9.19% | 9.69% | 10.64% | No phase |
| Water | 93.88% | 91.55% | 86.15% | No phase |
| Top phase Formic acid | 0.06% | 0.05% | 0.06% | 0.06% |
| 2-Butyl formate | 42.43% | 41.72% | 40.49% | 40.48% |
| 2-Butanol | 48.08% | 47.76% | 46.88% | 47.01% |
| Water | 10.63% | 10.71% | 10.53% | 10.55% |
| Bottoms comp. wt. % | | | | |
| Formic acid | 80.33% | 78.11% | 73.47% | 75.35% |
| 2-Butyl formate | N/D | N/D | N/D | N/D |
| 2-Butanol | N/D | N/D | N/D | N/D |
| Water | 22.08% | 22.15% | 24.65% | 21.94% |

Example 46—Distillation at 4.14 Bara

Example 43 was repeated except that the simulated 2-butyl formate hydrolysis effluent was fed to the column at 4.266 ml/min; the second feed was fed at 0.42 ml/min, and the reboiler residence time was about 2.5 hours. Over the course of the four-day operation, the reboiler temperature averaged about 155° C. Distillation results are given in Table 22. There was no evidence of formation of di-2-butyl ether. Overall conversion to free formic acid increased via passage through the distillation column from 43% in the hydrolysis effluent to 45-49% in the recovered formic acid/water bottoms stream.

TABLE 22

2-Butyl formate hydrolysis effluent distillation - Example 46

|  | Day 1 | Day 2 | Day 3 | Day 4 |
|---|---|---|---|---|
| Overall mass acc, % | 99.1% | 99.2% | 99.7% | 100.0% |
| Formate molar acc, % | 98.71% | 98.46% | 97.86% | 97.58% |
| 2-Butyl molar acc, % | 103.14% | 98.85% | 99.28% | 100.79% |
| Net % Free formic acid recovered in bottoms | 45.7% | 48.4% | 48.2% | 49.0% |
| Reflux ratio | 0.47 | 0.47 | 0.47 | 0.48 |
| Reboiler temperature, Celsius | 155.1 | 155.0 | 154.9 | 155.0 |
| Distillate bottom/ top phase mass ratio | 0.0006 | 0.0007 | 0.0006 | 0.0007 |
| Distillate comp. wt. % | | | | |
| Bottom phase Formic acid | 0.15% | 0.07% | 0.08% | 0.04% |
| 2-Butyl formate | 0.38% | 1.05% | 0.68% | 0.79% |
| 2-Butanol | 9.44% | 9.88% | 10.25% | 10.32% |
| water | 86.80% | 85.87% | 85.97% | 84.42% |
| Top phase Formic acid | 0.06% | 0.06% | 0.07% | 0.04% |
| 2-Butyl formate | 43.84% | 41.43% | 41.38% | 41.49% |
| 2-Butanol | 44.64% | 46.31% | 46.91% | 47.31% |
| water | 10.17% | 10.59% | 9.96% | 10.15% |
| Bottoms comp. wt. % | | | | |
| Formic acid | 78.61% | 78.64% | 76.23% | 75.99% |
| 2-Butyl formate | N/D | N/D | N/D | N/D |
| 2-Butanol | N/D | N/D | N/D | N/D |
| water | 20.77% | 22.53% | 21.58% | 22.13% |

Example 47—Distillation of Wet Alcohol Mixture to Produce Dry 2-Butanol

This experiment was carried out to determine effect of reflux ratio on the drying of 2-butanol by distillation of a formate mixture. Distillation operations were conducted in a column configuration comprising a silvered vacuum-jacketed Oldershaw trayed column of 2.54 cm ID (60 trays), a reboiler (flanged Hastelloy C276 pipe—3.81 cm ID, 46 cm length, approximately 200 ml at 100% fill for calibration of level controller); a silvered, vacuum-jacketed vapor take off line; and 50 ml glass reflux vessel. Heat was supplied to the reboiler by two 500-watt band heaters. Thermocouples were provided in the reboiler, vapor line, and ten thermocouples in the column section, roughly evenly spaced.

During distillation operation, the hydrolysis feed mixture was fed 60 cm above the 25-tray Oldershaw section into the packed section at a rate of 1 ml/min. An additional water feed of 0.082 ml/min water fed 210 cm above the Oldershaw section. The reflux pump was set to the desired rate, and the reboiler energy input adjusted to provide sufficient boilup to reach the target underflow temperature. The underflow take-off rate was adjusted by automatic control of reboiler level. The column was allowed to come to steady state operation (usually 10-24 hours). Cumulative distillate and bottoms samples were collected roughly every 24 hours, weighed, and sampled for GC analysis to determine overall mass accountability, top and bottom compositions, and reflux ratio as shown in Table 23. On all days of operation, the column head pressure was about 0.95-0.97 bara. Zero measurable water content in the bottoms stream was achieved on all days. Essentially all formic acid in the feed appeared in the bottoms product. The amount of 2-butanol co-distilled with the 2-butyl formate decreased as reflux ratio was increased.

TABLE 23

Wet alcohol distillation to produce dry 2-butanol - Example 47

|  | Day 1 | Day 2 | Day 3 | Day 4 | Day 5 |
|---|---|---|---|---|---|
| Overall mass acc., % | 99.3% | 95.3% | 97.9% | 95.6% | 99.3% |
| Reflux ratio | 1.3 | 1.6 | 1.7 | 1.3 | 1.1 |
| Reboiler temperature, Celsius | 112.7 | 113.0 | 114.1 | 110.1 | 107.8 |
| Distillate temperature, Celsius | 79.9 | 78.6 | 77.2 | 80.1 | 81.9 |
| Feed, grams | 1215.43 | 1212.14 | 1199.64 | 1187.15 | 1199.64 |
| Bottoms, grams | 248.52 | 368.61 | 428.83 | 231.78 | 105.07 |
| Distillate, Top phase, grams | 863.98 | 708.18 | 626.37 | 834.04 | 1036.21 |
| Distillate, bottom phase, grams | 74.61 | 79.67 | 122.68 | 71.80 | 47.96 |
| Feed, Formic acid, wt. % | 0.15% | 0.14% | 0.14% | 0.14% | 0.14% |
| 2-Butyl formate | 41.09% | 41.39% | 41.39% | 41.39% | 41.39% |
| 2-Butanol | 46.39% | 46.98% | 46.98% | 46.98% | 46.98% |
| Water | 10.86% | 9.36% | 9.36% | 9.36% | 9.36% |
| Distillate, top phase Formic acid wt. % | 0.00% | 0.00% | 0.00% | 0.00% | 0.00% |
| 2-Butyl formate | 57.55% | 62.26% | 76.21% | 57.82% | 47.22% |
| 2-Butanol | 34.51% | 30.79% | 19.27% | 34.57% | 42.77% |
| water | 5.50% | 4.82% | 2.40% | 5.69% | 7.76% |
| Distillate, bot phase, Formic acid wt. % | 0.26% | 0.29% | 0.30% | 0.12% | 0.05% |
| 2-Butyl formate | 0.18% | 0.17% | 0.24% | 0.54% | 0.61% |
| 2-Butanol | 8.49% | 8.42% | 6.98% | 7.52% | 8.41% |
| water | 90.10% | 92.23% | 93.00% | 89.31% | 89.30% |
| Bottoms comp, wt. % |  |  |  |  |  |
| Formic acid | 0.64% | 0.47% | 0.33% | 0.55% | 1.01% |
| 2-Butyl formate | 0.00% | 0.00% | 0.00% | 0.00% | 0.00% |
| 2-Butanol | 96.40% | 97.12% | 97.80% | 96.98% | 95.55% |
| water | 0.00% | 0.00% | 0.00% | 0.00% | 0.00% |

Other embodiments will be apparent to those skilled in the art from consideration of the specification and practice of the embodiments disclosed herein. It will be understood that variations and modifications can be effected within the spirit and scope of the disclosed embodiments. It is further intended that the specification and examples be considered as exemplary only, with a true scope and spirit of the disclosed embodiments being indicated by the following claims.

We claim:

1. A process for recovering formic acid from a formate ester mixture, wherein the process comprises,
    a) feeding the formate ester mixture, a hydrolysis recycle stream from step c), and water to a hydrolysis zone, wherein the formate esters mixture comprises a formate ester of an alcohol, hydrolyzing the formate ester of the alcohol, and removing a hydrolysis effluent comprising the formate ester of the alcohol, formic acid, and the alcohol;
    b) feeding the hydrolysis effluent to a distillation zone and removing a formic acid product and a wet alcohol mixture, wherein the formic acid product comprises greater than 75 wt. % formic acid and the wet alcohol mixture comprises the alcohol, water, the formate ester of the alcohol, and less than 0.5 wt. % formic acid; and
    c) feeding the wet alcohol mixture to an alcohol recovery zone and removing a dry alcohol stream and the hydrolysis recycle stream, wherein the dry alcohol stream comprises the alcohol and less than 1 wt. % water, and the hydrolysis recycle stream comprises water, the formate ester of the alcohol, and/or the alcohol,
    wherein the alcohol is selected from the group consisting of $C_3$ to $C_4$ alcohols.

2. The process of claim 1, wherein the formate ester mixture comprises at least 10 wt. % formate ester of the alcohol.

3. The process of claim 1, wherein t the alcohol is selected from the group consisting of iso-propanol, 2-butanol, and tert-butanol.

4. The process of claim 1, wherein a molar ratio of water:formate ester of the alcohol fed to the hydrolysis zone ranges from 0.5:1 to 3:1 and the hydrolysis zone operates at a temperature from 40° C. to 140° C. and at a pressure from 1 bara to 40 bara.

5. The process of claim 1, wherein the formic acid product comprises greater than 97 wt. % formic acid, the wet alcohol mixture comprises less than 500 ppm formic acid, and the dry alcohol stream comprises less than 500 ppm water.

6. The process of claim 1, wherein an overall conversion of the formate ester of the alcohol in the formate ester mixture to formic acid in the formic acid product ranges from 10% to 90%.

7. The process of claim 1, wherein the distillation zone comprises a first distillation column and wherein the process further comprises
    b1) feeding the hydrolysis effluent to the first distillation column and removing the wet alcohol mixture as a first distillate and a first bottoms comprising formic acid in an amount within 7 weight percentage points of an amount of formic acid in a formic acid/water azeotrope at an operating pressure of the first distillation column.

8. The process of claim 7, wherein the distillation zone further comprises a second distillation column and wherein the process further comprises
    b2) feeding the first bottoms to the second distillation column and removing the formic acid product as a second distillate and a second bottoms comprising formic acid in an amount within 5 weight percentage points of an amount of formic acid in a formic acid/water azeotrope at an operating pressure of the second distillation column; and b3) feeding the second bottoms to the first distillation column.

9. The process of claim 8, wherein the operating pressure of the first distillation column and the operating pressure of the second distillation column are set whereby the amount of formic acid in the formic acid/water azeotrope in the first distillation column is at least 10 weight percentage points higher than the amount of formic acid in the formic acid/water azeotrope in the second distillation column.

10. The process of claim 7, wherein the first bottoms comprises less than 0.1 wt. % formate ester of the alcohol.

11. The process of claim 1, wherein the alcohol recovery zone comprises a process selected from the group consisting of
- c1) azeotropic distillation wherein; when the alcohol is a $C_3$ alcohol, the azeotroping agent comprises the formate ester of the alcohol and/or an ether of the alcohol; and when the alcohol is a $C_4$ alcohol, the azeotroping agent comprises the formate ester of the alcohol, the ether of the alcohol, and/or the alcohol;
- c2) azeotropic distillation using an azeotrope agent comprising $C_5$-$C_6$ hydrocarbons, $C_1$-$C_3$ chlorinated hydrocarbons, and/or $C_4$-$C_8$ ethers; and
- c3) extractive distillation using an extractant comprising $C_2$-$C_4$ glycols and/or $C_4$-$C_6$ glycol ethers.

12. The process of claim 8, wherein the alcohol is selected from the group consisting of isopropanol and 2-butanol, further comprising using energy of condensing a first distillation column vapor to provide heat to one or more of the group consisting of the hydrolysis zone, the alcohol recovery zone, and the second distillation column.

13. A process for producing formic acid, wherein the process comprises,
- a) feeding carbon monoxide, a fresh feed, and a catalyst feed, to a carbonylation zone, wherein the fresh feed comprises an alcohol and the catalyst feed comprises a homogeneous catalyst, carbonylating the alcohol to produce a formate ester of the alcohol, and removing a carbonylation effluent comprising the formate ester of the alcohol, the alcohol, and the homogeneous catalyst;
- b) feeding the carbonylation effluent to a catalyst separation zone and removing a catalyst mixture and a formate ester mixture, wherein the catalyst mixture comprises the homogeneous catalyst and the alcohol, and the formate ester mixture comprises the formate ester of the alcohol;
- c) feeding the formate ester mixture, a hydrolysis recycle stream from step e), and water to a hydrolysis zone, hydrolyzing the formate ester of the alcohol, and removing a hydrolysis effluent comprising the formate ester of the alcohol, formic acid, and the alcohol;
- d) feeding the hydrolysis effluent to a distillation zone and removing a formic acid product and a wet alcohol mixture, wherein the formic acid product comprises greater than 75 wt. % formic acid and the wet alcohol mixture comprises the alcohol, water, the formate ester of the alcohol, and less than 0.5 wt. % formic acid; and
- e) feeding the wet alcohol mixture to an alcohol recovery zone and removing a dry alcohol stream and the hydrolysis recycle stream, wherein the dry alcohol stream comprises the alcohol and less than 1 wt. % water, and the hydrolysis recycle stream comprises water, the formate ester of the alcohol, and/or the alcohol, wherein the alcohol is selected from the group consisting of $C_3$ to $C_4$ alcohols.

14. The process of claim 13, wherein the alcohol is selected from the group consisting of iso-propanol, 2-butanol, and tert-butanol, and a molar ratio of water:formate ester of the alcohol fed to the hydrolysis zone ranges from 0.5:1 to 3:1, and the hydrolysis zone operates at a temperature from 40° C. to 140° C. and at a pressure from 1 bara to 40 bara.

15. The process of claim 13, wherein the distillation zone comprises a first distillation column and a second distillation column, wherein the process further comprises
- b1) feeding the hydrolysis effluent to the first distillation column and removing the wet alcohol mixture as a first distillate and a first bottoms comprising formic acid in an amount within 9 weight percentage points of an amount of formic acid in a formic acid/water azeotrope at an operating pressure of the first distillation column;
- b2) feeding the first bottoms to a second distillation column and removing the formic acid product as a second distillate and a second bottoms comprising formic acid in an amount within 7 weight percentage points of an amount of formic acid in a formic acid/water azeotrope at an operating pressure of the second distillation column; and
- b3) feeding the second bottoms to the first distillation column.

16. The process of claim 13, wherein the alcohol recovery zone comprises a process selected from the group consisting of
- c1) azeotropic distillation wherein; when the alcohol is a $C_3$ alcohol, the azeotroping agent comprises the formate ester of the alcohol and/or an ether of the alcohol; and when the alcohol is a $C_4$ alcohol, the azeotroping agent comprises the formate ester of the alcohol, the ether of the alcohol, and/or the alcohol;
- c2) azeotropic distillation using an azeotrope agent comprising $C_5$-$C_6$ hydrocarbons, $C_1$-$C_3$ chlorinated hydrocarbons, and/or $C_4$-$C_8$ ethers; and
- c3) extractive distillation using an extractant comprising $C_2$-$C_4$ glycols and/or $C_4$-$C_6$ glycol ethers.

17. A process for producing formic acid, wherein the process comprises,
- a) feeding methanol, a dry alcohol stream, and a catalyst recycle from step b) to a dehydrogenative coupling (DHC) zone, wherein the dry alcohol stream comprises an alcohol and less than 1 wt. % water, performing a DHC reaction of methanol with the alcohol to produce a formate ester of the alcohol, and removing a DHC effluent comprising the formate ester of the alcohol and a homogeneous catalyst;
- b) feeding the DHC effluent to a catalyst separation zone and removing the catalyst recycle and a formate ester mixture, wherein the catalyst recycle comprises the homogeneous catalyst and the formate ester mixture comprises the formate ester of the alcohol;
- c) feeding the formate ester mixture, a hydrolysis recycle stream from step e) and water to a hydrolysis zone, hydrolyzing the formate ester of the alcohol, and removing a hydrolysis effluent comprising the formate ester of the alcohol, formic acid, and the alcohol;
- d) feeding the hydrolysis effluent to a distillation zone and removing a formic acid product and a wet alcohol mixture, wherein the formic acid product comprises greater than 75 wt. % formic acid and the wet alcohol mixture comprises the alcohol, water, the formate ester of the alcohol, and less than 0.5 wt. % formic acid; and e) feeding the wet alcohol mixture to an alcohol recovery zone and removing the dry alcohol stream and the hydrolysis recycle stream, wherein the hydrolysis recycle stream comprises water, the formate ester of the alcohol, and/or the alcohol, wherein the alcohol is selected from the group consisting of iso-propanol, 2-butanol, and tert-butanol.

18. The process of claim 17, wherein the distillation zone comprises a first distillation column and a second distillation column, wherein the process further comprises b1) feeding the hydrolysis effluent to the first distillation column and removing the wet alcohol mixture as a first distillate and a first bottoms comprising formic acid in an amount within 9 weight percentage points of an amount of formic acid in a formic acid/water azeotrope at an operating pressure of the first distillation column;

b2) feeding the first bottoms to a second distillation column and removing the formic acid product as a second distillate and a second bottoms comprising formic acid in an amount within 7 weight percentage points of an amount of formic acid in a formic acid/water azeotrope at an operating pressure of the second distillation column; and b3) feeding the second bottoms to the first distillation column.

19. The process of claim 17, wherein the alcohol is 2-butanol and the alcohol recovery zone comprises a process selected from the group consisting of c1) azeotropic distillation using an azeotrope agent comprising 2-butanol, 2-butyl formate, and/or di-2-butyl ether;

c2) azeotropic distillation using an azeotrope agent comprising $C_5$-$C_6$ hydrocarbons, $C_1$-$C_3$ chlorinated hydrocarbons, and/or $C_4$-$C_8$ ethers; and c3) extractive distillation using an extractant comprising $C_2$-$C_4$ glycols and/or $C_4$-$C_6$ glycol ethers.

* * * * *